US009868960B2

(12) United States Patent
Sinha et al.

(10) Patent No.: US 9,868,960 B2
(45) Date of Patent: Jan. 16, 2018

(54) PLACENTAL LIKE ALKALINE PHOSPHATASE (PLAP) PROMOTER MEDIATED CELL TARGETING

(71) Applicants: DEPARTMENT OF BIOTECHNOLOGY, New Delhi (IN); NATIONAL BRAIN RESEARCH CENTRE, Haryana (IN); ALL INDIA INSTITUTE OF MEDICAL SCIENCES, New Delhi (IN)

(72) Inventors: Subrata Sinha, Haryana (IN); Imran Khan, New Delhi (IN); Mohammad Khalid Zakaria, New Delhi (IN); Kunzang Chosdol, New Delhi (IN); Parthaprasad Chattopadhyay, New Delhi (IN)

(73) Assignees: National Brain Research Centre, Haryana (IN); All India Institute of Medical Sciences, New Delhi (IN)

( * ) Notice: Subject to any disclaimer, the term of this patent is extended or adjusted under 35 U.S.C. 154(b) by 0 days.

(21) Appl. No.: 14/772,361

(22) PCT Filed: May 10, 2014

(86) PCT No.: PCT/IB2014/061350
§ 371 (c)(1),
(2) Date: Sep. 2, 2015

(87) PCT Pub. No.: WO2014/181314
PCT Pub. Date: Nov. 13, 2014

(65) Prior Publication Data
US 2016/0053279 A1  Feb. 25, 2016

(30) Foreign Application Priority Data
May 10, 2013  (IN) .......................... 1400/DEL/2013

(51) Int. Cl.
*C12N 15/52* (2006.01)
*C12N 15/85* (2006.01)
*A61K 48/00* (2006.01)
*C12N 15/11* (2006.01)
*C12N 15/63* (2006.01)
*C12N 15/113* (2010.01)

(52) U.S. Cl.
CPC .......... *C12N 15/85* (2013.01); *A61K 48/0058* (2013.01); *C12N 15/111* (2013.01); *C12N 15/1131* (2013.01); *C12N 15/63* (2013.01); *C12N 2320/32* (2013.01); *C12N 2330/51* (2013.01); *C12N 2830/008* (2013.01); *C12N 2830/15* (2013.01); *C12N 2830/85* (2013.01)

(58) Field of Classification Search
CPC ................ A61K 48/0058; C12N 15/52; C12N 2830/008
See application file for complete search history.

(56) References Cited

U.S. PATENT DOCUMENTS

2003/0035790 A1*  2/2003  Chen .................... A61K 38/208
                                                            424/85.2
2007/0166696 A1*  7/2007  Hahn ....................... C12N 7/00
                                                            435/4

OTHER PUBLICATIONS

Ahmed, Dissertation, University of Gottingen, Gottingen, Germany, 2001.*
Dean et al, Exp. Cell. Res. 253(2):713-722, 1999.*
GeneCard, ALPP; genecards.org; last accessed Jul. 25, 2016.*
GeneCard, ALPPL2; genecards.org; last accessed Jul. 22, 2016.*
International Search Report for PCT/IB2014/061350, Sep. 3, 2014, 11 pages.
Deng et al., Transcriptional Regulation of the Human Placental-like Alkaline Phosphatase Gene and Mechanisms Involved in Its Induction by Sodium Butyrate, American Association for Cancer Research, 7 pages, Jun. 15, 1992.
Wada et al., Characterization of Upstream Activation Elements Essential for the Expression of Germ Cell Alkaline Phosphatase in Human Choriocarcinoma Cells, The Journal of Biological Chemistry, vol. 268, No. 19, pp. 14003-14010, Jul. 6, 1993.
Lange et. al, Placental Alkaline Phosphatase as a Tumor Marker for Seminoma, Cancer Research Journals, Nov. 9, 2015, vol. 42, pp. 3244-3247.
Kaneko et al., Adenovirus-mediated Gene Therapy of Hepatocellular Carcinoma Using Cancer-specific Gene Expression, Cancer Research Journals, Nov. 15, 1995, vol. 55, pp. 5283-5287.
Peng et al., Alpha-Fetoprotein Promoter-Driven Cre/LoxP-Switched RNA Interference for Hepatocellular Carcinoma Tissue-Specific Target Therapy, PLoS ONE, Feb. 2013, vol. 8, Issue 2, pp. 1-12.
Adrian L. Harris, Antiangiogenesis for cancer therapy, The Lancet, May 1997, vol. 349, pp. 13-15.
Morris et al., Bidirectional Transcription Directs Both Transcriptional Gene Activation and Suppression in Human Cells, PLoS Genetics, Nov. 2008, vol. 4, Issue 11, pp. 1-9.
Graulich et al., Cell type specificity of the human endoglin promoter, Gene Journal, 1999, vol. 227, pp. 55-62.
Wang et al., Characterization of Hypoxia-inducible Factor 1 and Regulation of DNA Binding Activity by Hypoxia, The Journal of Biological Chemistry, Oct. 15, 1993, vol. 268, No. 29, pp. 21513-21518.
Mehndiratta et al., CpG Hypermethylation of the C-myc Promoter by dsRNA Results in Growth Suppression, Molecular Pharmaceutics, 2011, vol. 8, pp. 2302-2309.

(Continued)

*Primary Examiner* — Kevin Hill
(74) *Attorney, Agent, or Firm* — Robert D. Fish; Fish IP Law, LLC

(57) ABSTRACT

The present invention relates to cell specific therapeutic modality by using a region of the PLAP Promoter. The invention further relates to specific expression of therapeutically PLAP useful sequences for specific transcriptional activation of this gene. The invention also relates to the PLAP region which may be used alone or in combination with other regions like enhancer sequences that augment cell or tumour specific gene expression.

11 Claims, 19 Drawing Sheets

(56) References Cited

OTHER PUBLICATIONS

Wright et al., Telomerase activity in human germline and embryonic tissues and cells, Developmental Genetics, Jan. 1996, vol. 18, pp. 173-179.

Jaggar et al., Endothelial Cell-Specific Expression of Tumor Necrosis Factor-a from the KDR or E-Selection Promoters Following Retroviral Delivery, Human Gene Therapy, Dec. 10, 1997, vol. 8, pp. 2239-2247.

Pugh et al., Functional analysis of an oxygen-regulated transcriptional enhancer lying 3' to the mouse erythropoietin gene, Proc. Natl. Acad. Sci., Dec. 1991, vol. 88, pp. 10553-10557.

Ido et al., Gene Therapy Targeting for Hepatocellular Carcinoma: Selective and Enhanced Suicide Gene Expression Regulated by a Hypoxia-inducible Enhancer Linked to a Human a-Fetoprotein Promoter, Cancer Research Journal, Apr. 1, 2001, vol. 61, pp. 3016-3021.

Marais et al., Gene-directed Enzyme Prodrug Therapy with a Mustard Prodrug/Carboxypeptidase G2 Combination, Cancer Research Journal, Oct. 15, 1996, vol. 56, pp. 4735-4742.

Eaton et al., Genetic prodrug activation therapy (GPAT) in two rat prostate models generates an immune bystander effect and can be monitored by magnetic resonance techniques, Gene Therapy, 2001, vol. 8, pp. 557-567.

Huber et al., Virus-Directed Enzyme/Prodrug Therapy (VDEPT) Selectively Engineering Drug Sensitivity into Tumors, Annals New York Academy of Sciences, pp. 104-114, Downloaded on Dec. 15, 2015.

Maxwell et al., Hypoxia-inducible factor-1 modulates gene expression in solid tumors and influences both angiogenesis and tumor growth, Proc. Natl. Acad. Sci., Jul. 1997, vol. 94, pp. 8104-8109.

Fishman et al., Immunology and Biochemistry of Regan Isoenzyme of Alkaline Phosphatase in Human Cancer, Nature Publishing Group, Aug. 17, 1968, vol. 219, pp. 697-699.

Lan et al., In Vivo Selective Gene Expression and Therapy Mediated by Adenoviral Vectors for Human Carcinoembryonic Antigen-producing Gastric Carcinoma, Cancer Research Journal, Oct. 1, 1997, vol. 57, pp. 4279-4284.

Jose Luis Millan, Mammalian Alkaline Phosphatases, Biology to Applications in Medicine and Biotechnology, 2006, pp. 1-339.

Nathanson et al., New Observations on the Kegan Isoenzyme of Alkaline Phospi-Iatase in Cancer Patients, Jun. 1971, No. 6, pp. 1388-1397.

J. Folkman, New Perspectives in Clinical Oncology from Angiogenesis Research, European Journal of Cancer, 1996, vol. 32A, No. 14, pp. 2534-2539.

Kevin V. Morris, Non-coding RNAs, epigenetic memory and the passage of information to progeny, National Institutes of Health, Jul. 2009, vol. 6, No. 3, 99. 242-247.

Napoli et al., Promoter-specific transcriptional interference and c-myc gene silencing by siRNAs in human cells, The EMBO Journal, 2009, vol. 28, pp. 1708-1719.

Latham et al., Prostate-specific Antigen Promoter/Enhancer Driven Gene Therapy for Prostate Cancer: Construction and Testing of a Tissue-specific Adenovirus Vector, Cancer Research Journal, vol. 60, pp. 334-341.

Palanichamy et al., Silencing of Integrated Human Papillomavirus-16 Oncogenes by Small Interfering RNA—Mediated Heterochromatization, American Association for Cancer Research, Jul. 2010, vol. 9, No. 7, pp. 2114-2122.

Wierstra et al., The c-myc Promoter: Still MysterY and Challenge, Advances in Cancer Research, 2008, pp. 113-333.

Dachs et al., The molecular response of mammalian cells to hypoxia and the potential for exploitation in cancer therapy, British Journal of Cancer,1996, vol. 74, pp. S126-S132.

Su et al., Tissue-specific expression of herpes simplex virus thymidine kinase gene delivered by adeno-associated virus inhibits the growth of human hepatocellular carcinoma in athymic mice, Proc. Natl. Acad. Sci., Dec. 1997, vol. 94, pp. 13891-13896.

Smotkin et al., Transcription of human papillomavirus type 16 early genes in a cervical cancer and a cancer-derived cell line and identification of the E7 protein, Proc. Natl. Acad. Sci., Jul. 1986, vol. 83, pp. 4680-4684.

Harrington et al., Transcriptional control: an essential component of cancer gene therapy strategies?, Advanced Drug Delivery Reviews, Jun. 2000, vol. 44, pp. 167-184.

Deng et al., Transcriptional Regulation of the Human Placental-like Alkaline Phosphatase Gene and Mechanisms Involved in Its Induction by Sodium Butyrate, Cancer Research Journal, Jun. 15, 1992, vol. 52, pp. 3378-3383.

Xing et al., Tumor cell-specific blockade of CXCR4/SDF-1 interactions in prostate cancer cells by hTERT promoter induced CXCR4 knockdown: A possible metastasis preventing and minimizing approach, Cancer Biology & Therapy, Nov. 2008, vol. 7, No. 11, pp. 1839-1848.

Brand et al., Tumor cell-specific transgene expression prevents liver toxicity of the adeno-HSVtk/GCV approach, Gene Therapy, 1998, vol. 5, pp. 1363-1371.

Qiao et al., Tumor-specific transcriptional targeting of suicide gene therapy, Gene Therapy, 2002, vol. 9, pp. 168-175.

Sasaki et al., Ultrastructural Studies on Regan and Non-Regan Isoenzymes of Alkaline Phosphatase in Human Ovarian Cancer Cells, Cancer Research Journal, Nov. 1973, vol. 33, pp. 3008-3018.

\* cited by examiner

AAGCTGCCTTTCTCAGGACCCCAGCCCCAGCCCAGCCCAGCCACACCCTGCGACT
CTCTTCAGCCAGTGTGGCTTCAGGTCAAGAGGCTGGGCGGGGTCAAGGTGGTAA
CAAGGGGAGGGGCCAGGACACAGTTTTCCCTGATTTAAACCCAGGCAGCCTGGA
GTGCAGCTCATACTCCATACCTGGGATTTCCGC

Figure 1

GGGAATTTCCGGGAATTTCCGGGAATTTCCGGGAATTTCCAAGCTGCCTTTCT
CAGGACCCCAGCCCCAGCCCAGCCCAGCCACACCCTGCGACTCTCTTCAGCCAGT
GTGGCTTCAGGTCAAGAGGCTGGGCGGGGTCAAGGTGGTAACAAGGGGAGGGG
CCAGGACACAGTTTTCCCTGATTTAAACCCAGGCAGCCTGGAGTGCAGCTCATAC
TCCATACCTGGGATTTCCGC

Figure 2

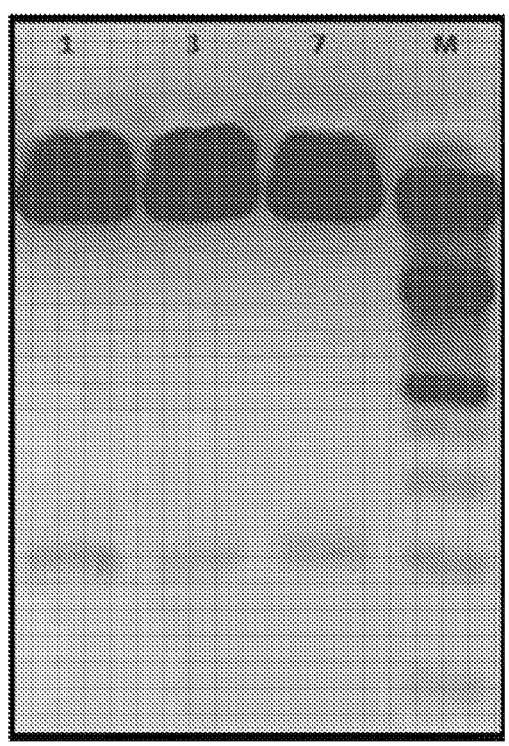 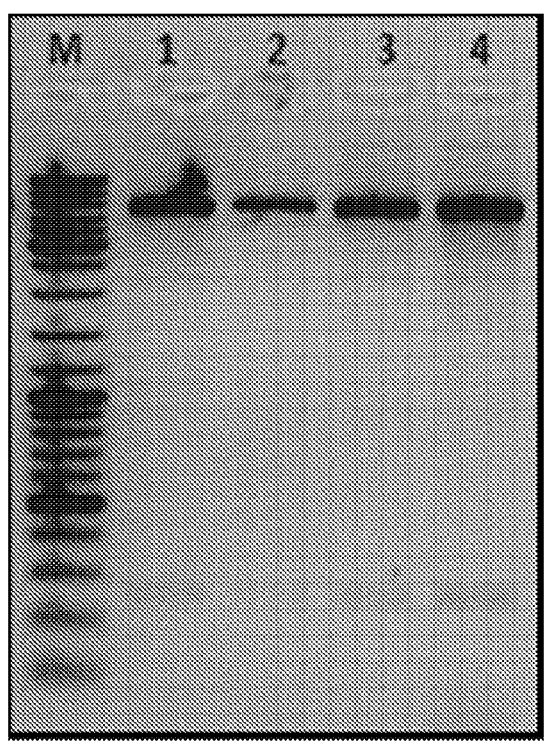
(A) (B)
Figure 5

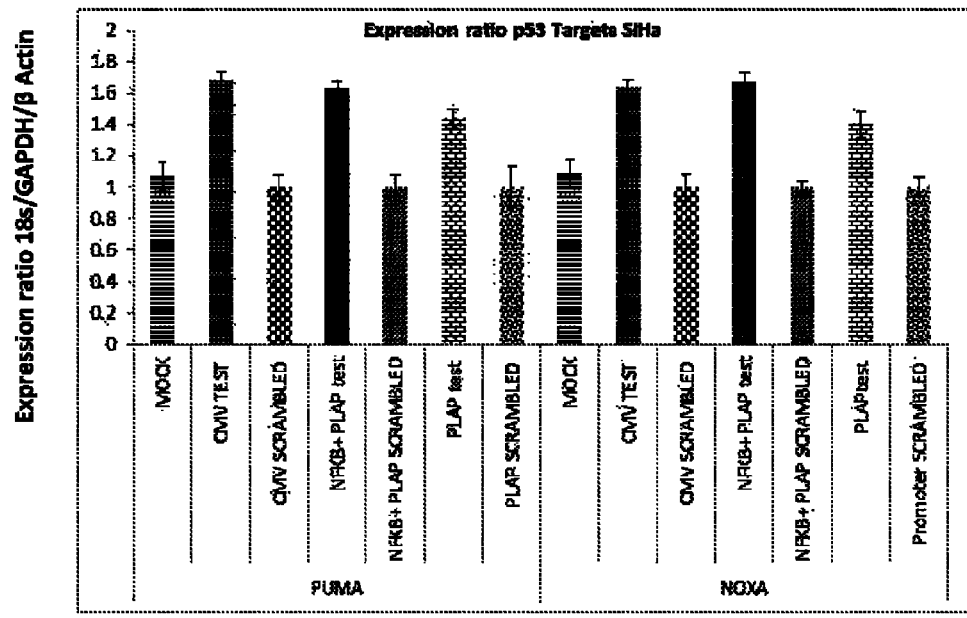
(A)
p53 Western Blotting in SiHa
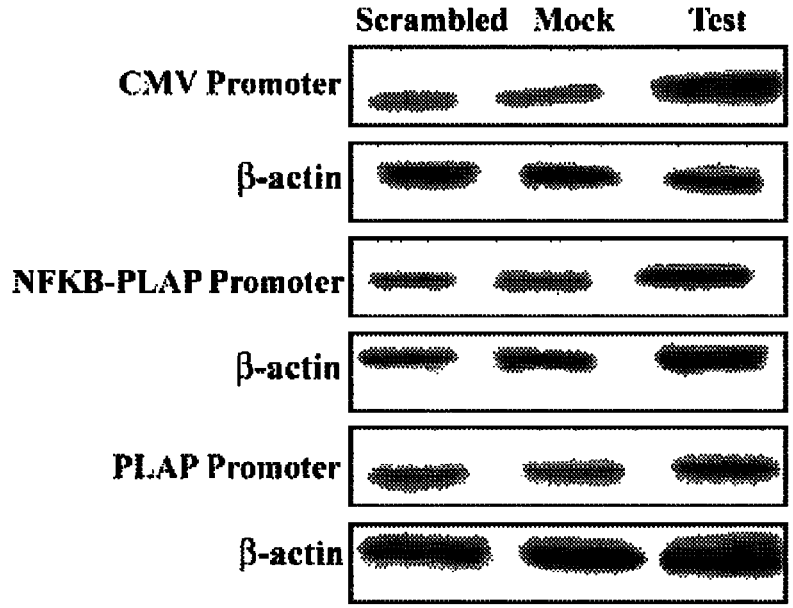
(B)
Figure 9

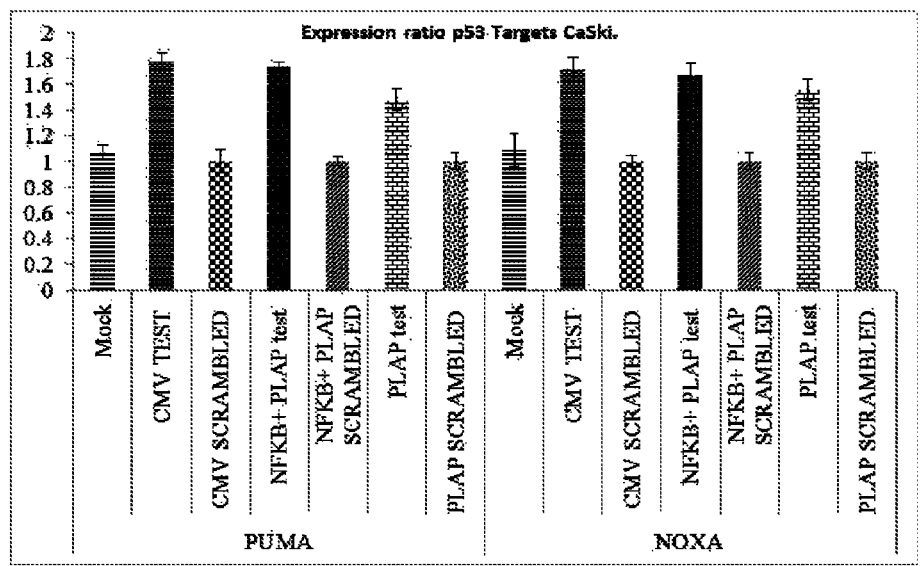
(A)
p53 Western Blotting in Caski
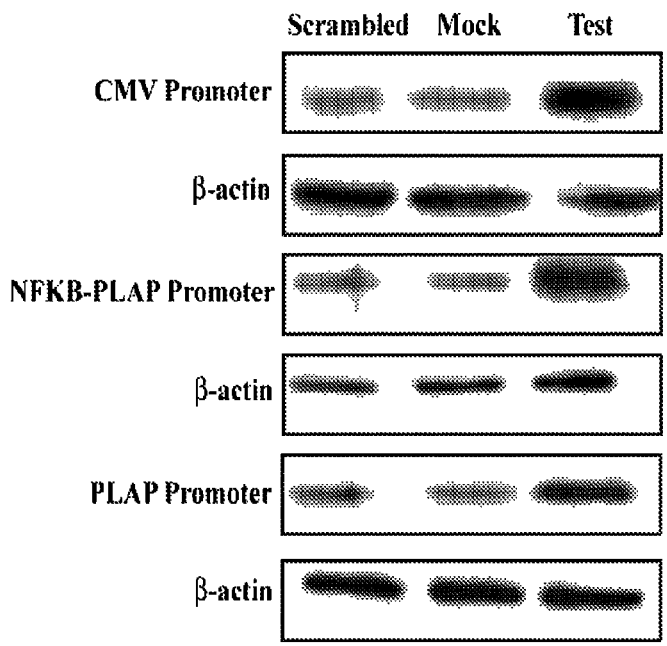
(B)
Figure 10

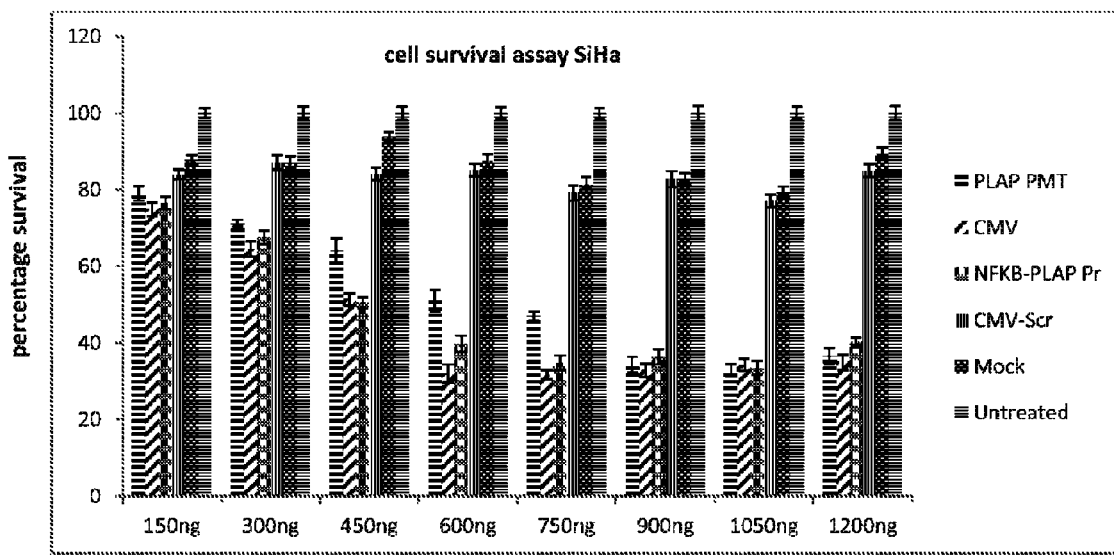
(A)
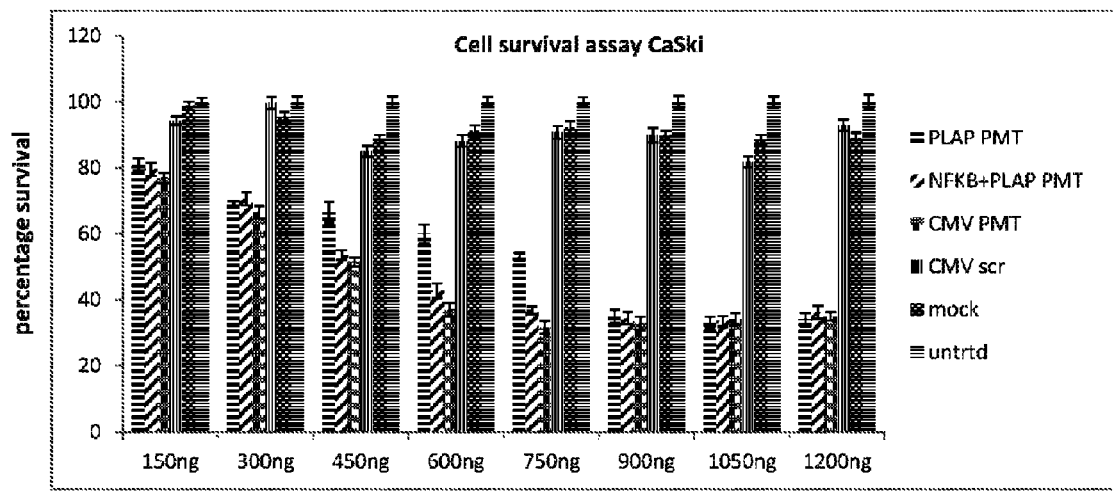
(B)
Figure 11

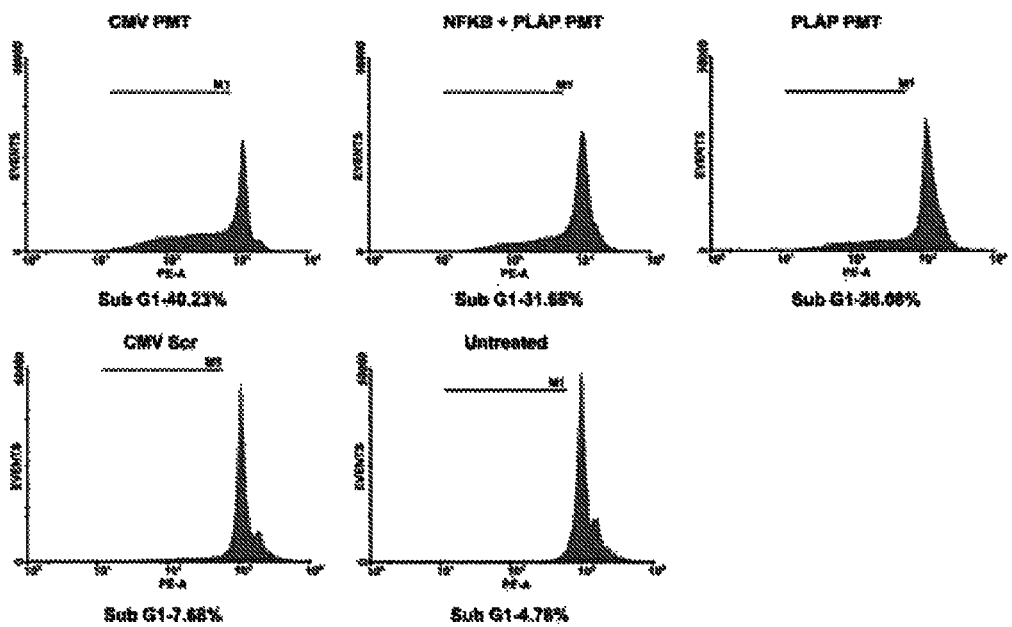
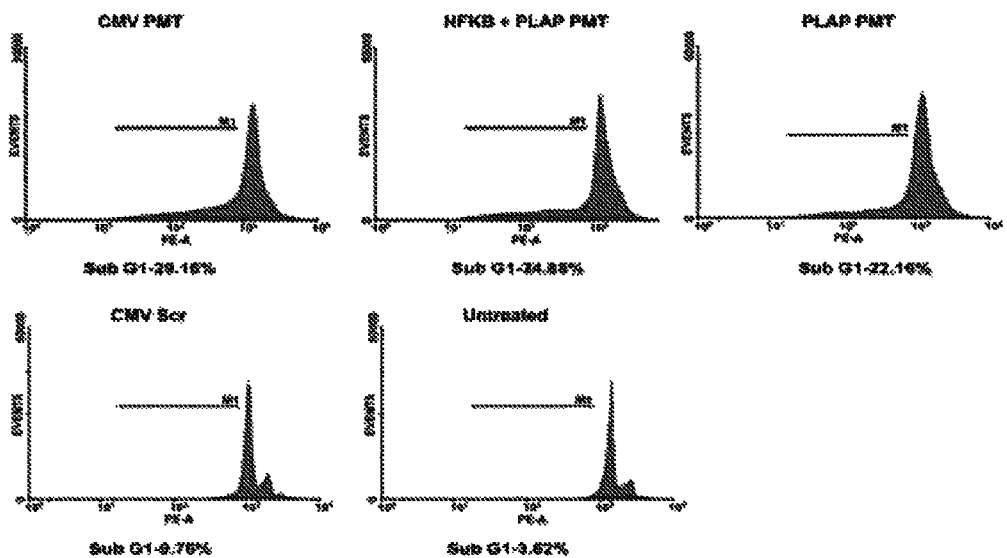
Figure 12

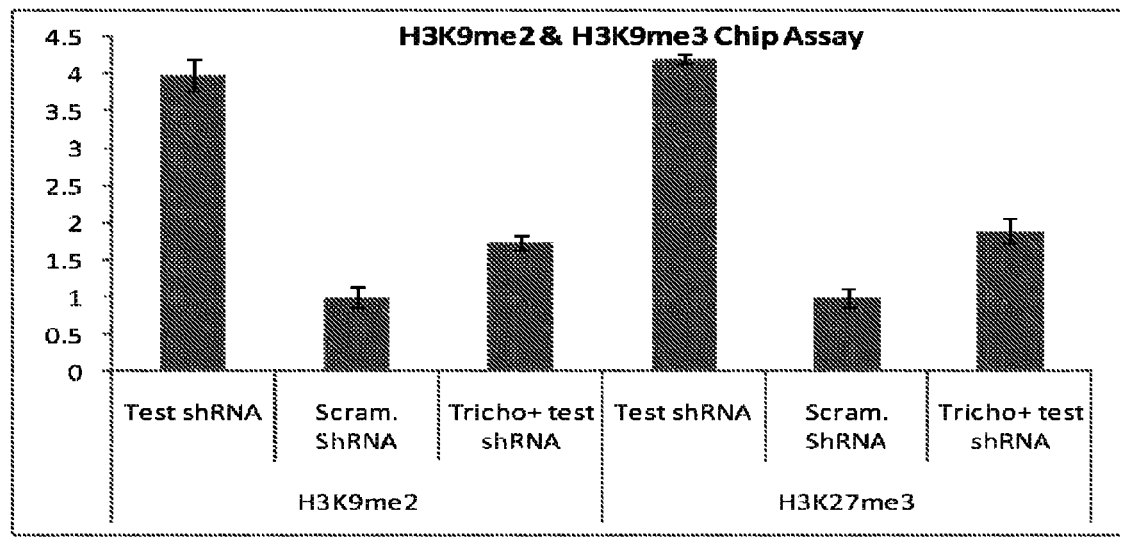
(A)
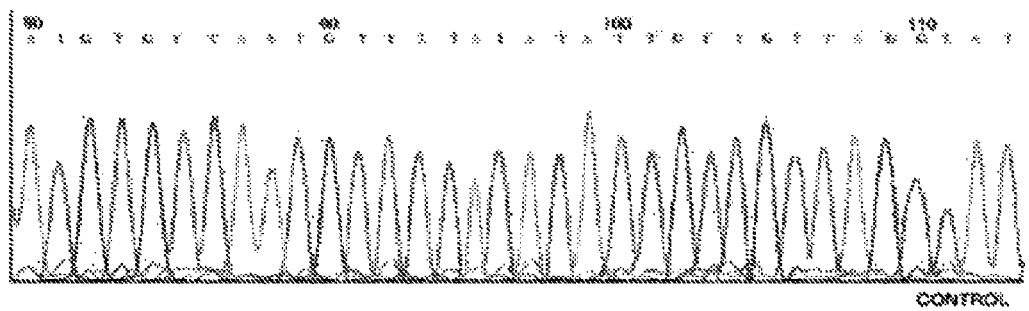
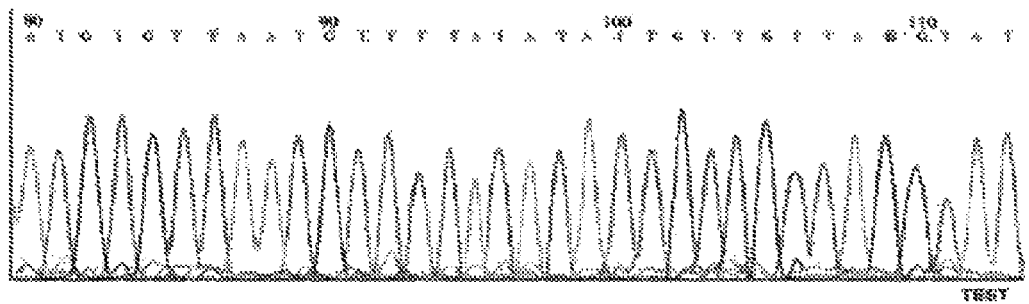
(B)
Figure 13

CTAATGGTGACAGGGGGAATGGCAAGCAAGTGGGATCAGAAGGGTATGGACA
TTGCCTATGAGGAGGCGGCCTTAGGTTACAAAGAGGGTGGTGTTCCTATTGGCGG
ATGTCTTATCAATAACAAAGACGGAAGTGTTCTCGGTCGTGGTCACAACATGAG
ATTTCAAAAGGGATCCGCCACACTACATGGTGAGATCTCCACTTTGGAAAACTGT
GGGAGATTAGAGGGCAAAGTGTACAAAGATACCACTTTGTATACGACGCTGTCT
CCATGCGACATGTGTACAGGTGCCATCATCATGTATGGTATTCCACGCTGTGTTG
TCGGTGAGAACGTTAATTTCAAAAGTAAGGGCGAGAAATATTTACAAACTAGAG
GTCACGAGGTTGTTGTTGACGATGAGAGGTGTAAAAAGATCATGAAACAAT
TTATCGATGAAAGACCTCAGGATTGGTTTGAAGATATTGGTGAGTAGAGCACG
CA (A)

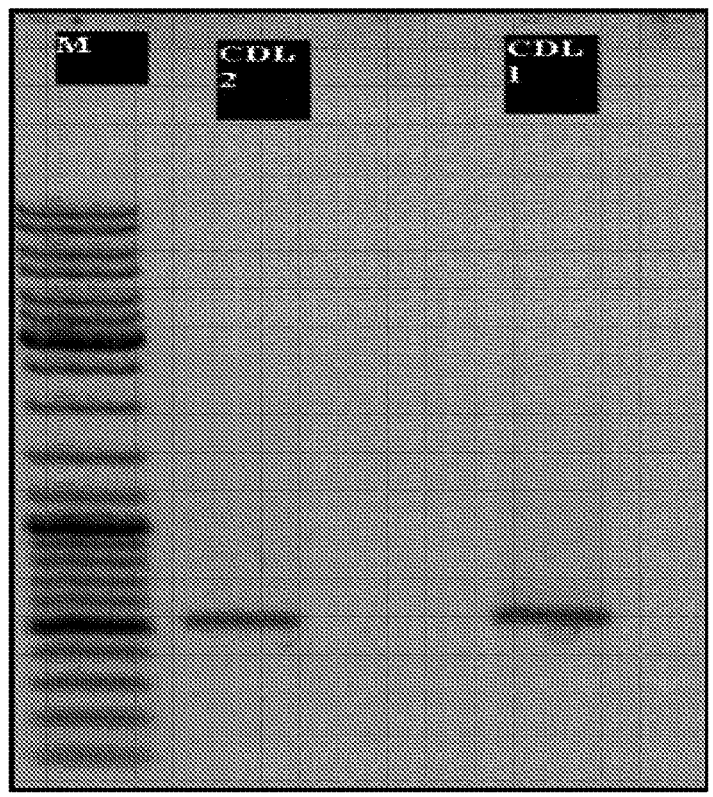

(B)

Figure 14 (a and b)

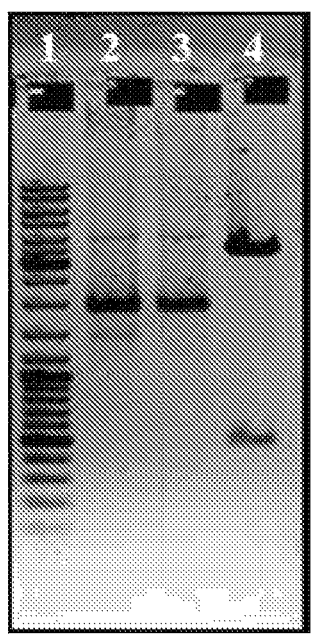
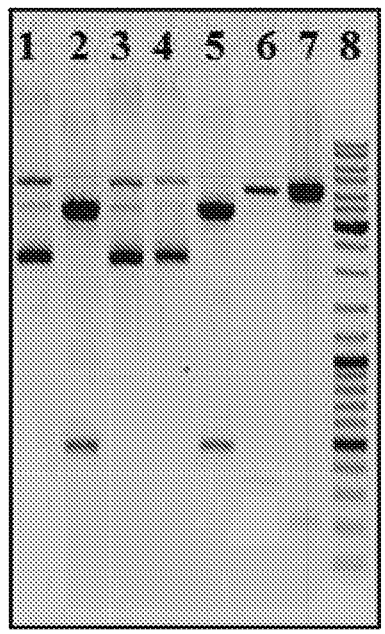
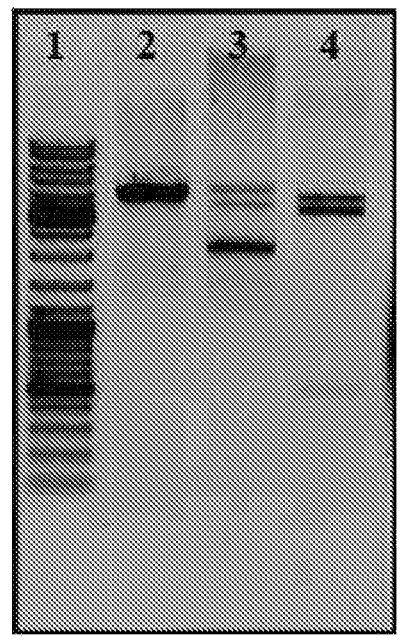
(1)　　　　　　　　(2)　　　　　　　　(3)
Figure 14 (c) (continued)

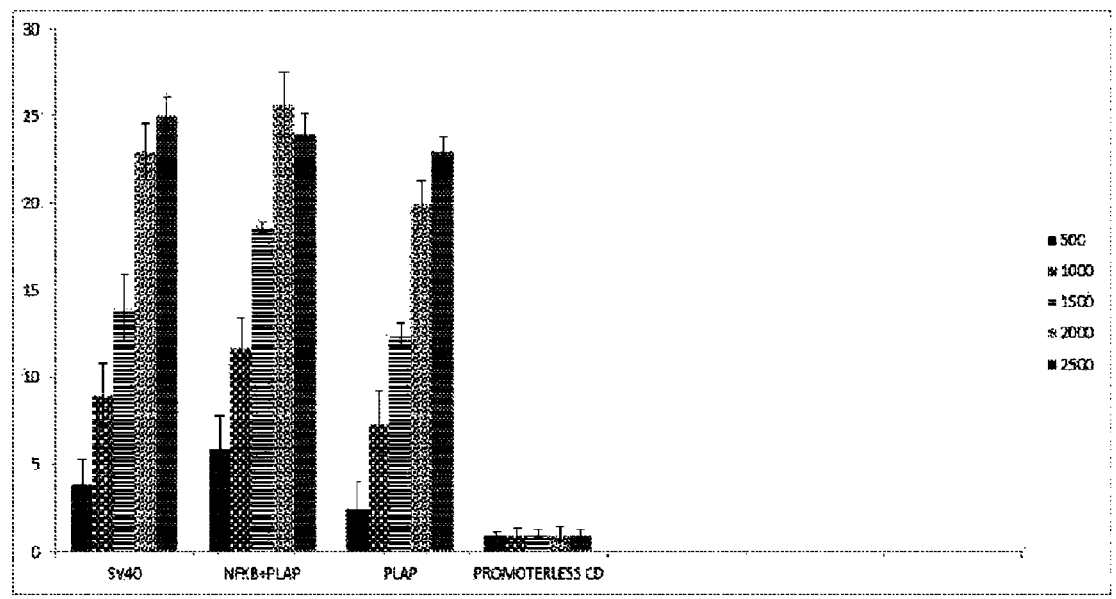
(A)
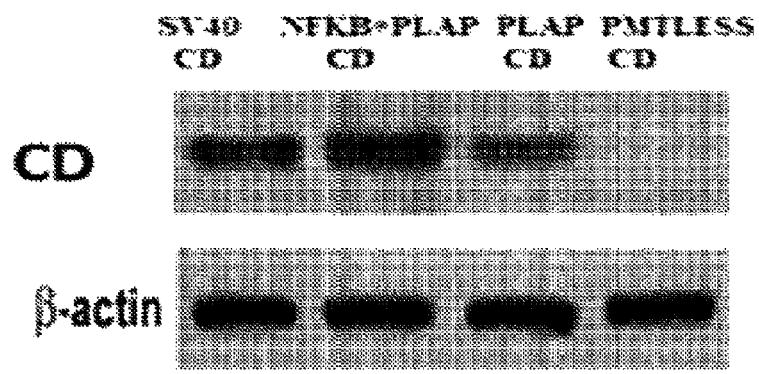
(B)
Figure 15

SEQUENCE LISTING

```
<160> NUMBER OF SEQ ID NOS: 3

<210> SEQ ID NO 1
<211> LENGTH: 196
<212> TYPE: DNA
<213> ORGANISM: Homo sapiens
<220> FEATURE:
<221> NAME/KEY: DNASequence
<222> LOCATION: (1)..(196)
<223> OTHER INFORMATION: Unique PLAP promoter Sequence

<400> SEQUENCE: 1
aagctgcctt tctcaggacc ccagccccag cccagcccag ccacaccctg cgactctctt      60
cagccagtgt ggcttcaggt caagaggctg ggcggggtca aggtggtaac aaggggaggg     120
gccaggacac agtttccct gatttaaacc caggcagcct ggagtgcagc tcatactcca      180
tacctgggat ttccgc                                                     196

<210> SEQ ID NO 2
<211> LENGTH: 236
<212> TYPE: DNA
<213> ORGANISM: Artificial Sequence
<220> FEATURE:
<223> OTHER INFORMATION: Enhancer (NFKB)-Promoter (PLAP) Sequence.

<400> SEQUENCE: 2
gggaatttcc gggaatttcc gggaatttcc gggaatttcc aagctgcctt tctcaggacc      60
ccagccccag cccagcccag ccacaccctg cgactctctt cagccagtgt ggcttcaggt     120
caagaggctg ggcggggtca aggtggtaac aaggggaggg gccaggacac agtttccct      180 gatttaaacc caggcagcct ggagtgcagc tcatactcca tacctgggat ttccgc         236

<210> SEQ ID NO 3
<211> LENGTH: 488
<212> TYPE: DNA
<213> ORGANISM: Saccharomyces cerevisiae
<220> FEATURE:
<221> NAME/KEY: Nucleotide
<222> LOCATION: (1)..(488)
<223> OTHER INFORMATION: Yeast cytosine deaminase sequence

<400> SEQUENCE: 3
ctaatggtga caggggggaat ggcaagcaag tgggatcaga agggtatgga cattgcctat     60
gaggaggcgg ccttaggtta caaagagggt ggtgttccta ttggcggatg tcttatcaat    120
aacaaagacg gaagtgttct cggtcgtggt cacaacatga gatttcaaaa gggatccgcc    180
acactacatg gtgagatctc cactttggaa aactgtggga gattagaggg caaagtgtac    240
aaagatacca ctttgtatac gacgctgtct ccatgcgaca tgtgtacagg tgccatcatc    300
atgtatggta ttccacgctg tgttgtcggt gagaacgtta atttcaaaag taagggcgag    360
aaatatttac aaactagagg tcacgaggtt gttgttgttg acgatgagag gtgtaaaaag    420
atcatgaaac aatttatcga tgaaagacct caggattggt ttgaagatat tggtgagtag    480
agcacgca                                                              488
```

PLACENTAL LIKE ALKALINE PHOSPHATASE (PLAP) PROMOTER MEDIATED CELL TARGETING

FIELD OF INVENTION

The present invention relates to cell specific therapeutic modality by using a region of the PLAP Promoter. The invention further relates to specific expression of therapeutically useful sequences for specific transcriptional activation under PLAP promoter. The invention also relates to the PLAP region which may be used alone or in combination with enhancer response element sequences that augment cell or tumour specific gene expression.

BACKGROUND OF THE INVENTION

Although all cells of one organism contain more or less the same genetic information, genes are turned on and others are turned off at different locations and times during the life cycle of an organism. The intricate pattern of gene regulation involves molecular signals that act on DNA sequences encoding protein products. Such a DNA sequence that facilitates the transcription of a particular gene is called a promoter. The promoter is the main determinant for the initiation of transcription and modulation of levels and timing of gene expression.

Certain promoters are either silent or active at very low background levels in normal tissues but highly active in tumors. A number of promoters can be included within this rather heterogeneous group:

(1) Promoters which are specific for the malignant process but which show no particular tissue specificity—so-called "cancer specific promoters".
(2) Promoters of genes which encode onco-fetal antigens and which have very well-defined patterns of tissue specificity—so-called "tumor-type specific promoters".
(3) Promoters responsive to patho-physiological conditions which predominate in tumor areas (e.g. hypoxia responsive promoters),
(4) Promoters which are specific to the tumor vascular endothelium.

Cancer Specific Promoters

Certain genes are up regulated as part of the malignant phenotype in a range of tumours in a tissue non-specific manner. The promoters of such genes potentially represent powerful targets because they may provide a means of targeting therapeutic genes to a variety of malignant tissues. This raises the possibility of constructing generic cancer specific vectors, which will be applicable across a broad range of oncological practice, without the need to tailor design of the promoters used on an individual, patient by patient, basis.

Telomerase is not expressed in normal tissues (except germ cells and stem cells), but is abnormally reactivated in all major cancer types (Buys, C. H. 2000, N. Engl. J. Med. 342, 1282-1283.; Shay, J. W. 1998, Cancer J. Sci. Am. 4 Suppl 1, S26-34). Telomerase enables tumour cells to maintain telomere length, thus circumventing the process of senescence. Many cancer cell lines can be passaged indefinitely and are considered immortal, whereas normal cells senescence after a set number of population doublings called the Hayflick limit. Telomerase expression has been reported in the vast majority of cancers and its promoter has been utilised for cancer therapeutics both by RNA interference approaches as well as gene suiciding approaches (Plumb et al., 2001, Oncogene 20, 7797-7803; Xing et al., 2008, Cancer Biol. Ther. 7, 1839-1848). However, It should be borne in mind that there still exists the possibility of germ line or stem cell toxicity with this strategy as telomerase activity is reported in such cellular systems (Wright et al., 1996, Dev. Genet. 18, 173-179). This limits the applications of telomerase promoter for targeted cancer therapeutics as it can elicit its effects within untransformed or normal cellular machinery too.

Tumour-Type Specific Promoters

Onco-fetal antigens are proteins which are expressed during fetal life as a part of normal development and are silenced in the adult. These proteins can be re-expressed in certain malignant conditions. The classical examples are carcinoembryonic antigen (CEA), which is expressed by a number of adenocarcinomas including colorectal, breast and lung cancers, and alpha fetoprotein (AFP), which is expressed by hepatocellular carcinomas and malignant testicular teratomas (Harrington et al., 2000, Adv. Drug Deliv. Rev. 44, 167-184). The promoters of these genes have been characterized and their essential elements have been identified.

A number of authors have used the CEA promoter to the drive expression of either reporter or therapeutic genes in gastric, lung and colorectal tumour systems (Cao et al., 1999, Gene Ther. 6, 83-90.). In most of these studies, adeno virus (AV) vectors have been used with the CEA promoter controlling the expression of a suicide gene. Such vectors have been shown to confer selective gene expression both in vitro and in vivo after intra-peritoneal (Lan et al., 1997, Cancer Res. 57, 4279-4284) or intra-tumoral injection (Brand et al., 1998, Gene Ther. 5, 1363-1371). A similar body of work exists for the treatment of hepatonma with AFP-regulated gene therapy systems (Su et al., 1997, Proc. Natl. Acad, Sci. U.S.A 94, 13891-13896). Impressive in vitro viral replication and toxicity were seen with hepatoma cell lines and these data translated to tumour responses in subcutaneous hepatomas (but not non-hepatomas) in nude mice (Arbuthnot et al., 1996, Hum. Gene Ther. 7, 1503-1514; Kaneko et al., 1995, Cancer Res. 0.55, 5283-5287).

Promoters Specific to Cancer Pathophysiology

Cellular hypoxia induces a stress response in which the expression of many genes is increased. Not surprisingly, a common underlying theme to the functions of these genes is to promote processes which will relieve hypoxia, such as short-term measures like shifting the emphasis of cellular respiration towards the glycolytic pathway and longer-term responses like increasing erythropoiesis and angiogenesis (Dachs and Stratford, 1996, Br. J. Cancer. Suppl. 27, S126-132), The genes that mediate these adaptive responses phosphoglycerate kinase 1, erythropoietin (Epo) and vascular endothelial growth factor (VEGF) genes, respectively all have promoters which contain cis-acting hypoxia response elements (HRE) which are capable of binding either hypoxia inducible factor 1 (HIF-1) or other related proteins (Maxwell et al., 1997, Proc. Natl. Acad. Sci. U.S.A 94, 8104-8109; Pugh et al., 1991, Proc. Natl. Acad. Sci, U.S.A 88, 10553-10557; Wang and Semenza, 1993, J. Biol. Chem. 268, 21513-21518). In normal healthy tissue, hypoxia is rare, perhaps with the exception of some cartilaginous tissues. However, hypoxia, often to a profound degree, is a common feature in many solid tumours and is thought to play a significant role in the resistance of cancer to ionising radiation and cytotoxic chemotherapy. The use of promoter elements responsive to tissue hypoxia in gene therapy strategies offers the prospect of turning the tables on the tumour and using this treatment-resistant pathophysiological state to drive the expression of therapeutic genes (Dachs et al., 1997, at. Med. 3, 515-520).

Endothelium-Specific Promoters

In the last 20 years, there has been an increasing appreciation of the central role played by the tumour vasculature in the progression and dissemination of malignant disease (Folkman, 1996, Eur. J. Cancer Oxf. Engl. 1990 32A, 2534-2539). It is clear that in order to increase beyond a certain size limit, a tumour must recruit an adequate blood supply. It does this, at least in part, by stimulating the ingress of new blood vessels by secreting angiogenic factors such as VEGF or by causing them to be secreted by stromal cells. As a consequence of these observations, the tumour neo-vasculature has become a legitimate target of cancer gene therapy (Harris, 1997, Lancet 349 Suppl 2, SII13-15). The attraction of destroying the tumour neovasculature is that it offers the prospect of killing a large number of dependent tumour cells through a form of anatomical bystander effect. In recent years, a number of genes, which are up-regulated in the proliferating endothelium of tumour blood vessels, have been identified. Jaggar et al., (1997, Hum. Gene Ther. 8, 2239-2247) reported that proximal elements from both the VEGF responsive kinase insert domain receptor (KDR) and the E-selectin promoters are capable of directing endothelial cell specific gene expression. Walton et al., 1998 used an adenoviral vector in which a luciferase reporter was under the transcriptional control of the E-selectin promoter. High levels of reporter gene expression were reported in endothelial cells in a fashion that was upregulated on exposure to either TNF-α or tumour-conditioned medium. There was little gene expression in non-endothelial tissues. Another gene that has been shown to be overexpressed in tumour vasculature is endoglin (a member of the transforming growth factor beta receptor complex). Graulich et al., (1999, Gene 227, 55-62) have identified its promoter and demonstrated that it shows significant tissue specificity and greater strength than the SV40 promoter in endothelial cells (HU-VEC, HMVEC and ECV304 cells) as compared to fibroblasts or epithelial cells.

A number of promoters have already been investigated with positive results: for example, α-fetoprotein (AFP) promoter to target hepatocellular carcinoma (Ido et al., 2001, Cancer Res. 61, 3016-3021), prostate-specific antigen (PSA) to target prostate cancer (Latham et al., 2000a, Cancer Res. 60, 334-341) and so on.

Several examples showed that the use of enhancers in conjunction with specific promoters in viral constructs might be beneficial. Placing a 1455-bp PSA-enhancer sequence upstream of either the PSA or the glandular kallicrein promoter (hKLK2) increased the expression of the marker gene in the PSA-positive prostate cancer cell line LNCaP by 20-fold. Tandem duplication of the PSA enhancer increased expression to 50-fold while retaining tissue specificity (Ido et al., 2001, Cancer Res. 61, 3016-3021; Latham et al., 2000, Cancer Res. 60, 334-341).

Transcriptional Gene Silencing (TGS) refers to using siRNA to target the enhancer or promoter regions of genes thereby leading to the downregulation of their expression. These siRNAs have been shown to repress gene expression by DNA methylation or Histone methylation (Morris, 2009 RNA Biol. 6, 242-247; Morris et al., 2004 Science 305, 1289-1292; Morris et al. 2008, PLoS Genet. 4, e1000258; Napoli et al., 2009, EMBO J. 28, 1708-1719).

HPV is central to the development of cervical neoplasia, with HPV 16 being the most prevalent in squamous cell carcinoma and HPV 18 most prevalent in adenocarcinoma (Alani and Münger, 1998, J. Clin. Oncol. Off. J. Am. Soc. Clin. Oncol. 16, 330-337). The E6 and E7 oncoproteins are the main transforming genes of oncogenic strains of HPV. The HPV E7 protein acts primarily by binding to and inactivating the retinoblastoma (Rb) tumor suppressor gene product (Smotkin and Wettstein, 1986, Proc. Natl. Acad. Sci. U.S.A. 83, 4680-4684). The E6 proteins of oncogenic HPV subtypes binds to and inactivate the p53 tumor suppressor gene product. Both E6 & E7 are governed by a common promoter/enhancer region, so targeting this common region by Transcriptional Gene Silencing (TGS) could be used as more potent tool to tackle HPV-16 associated cervical cancer as this would result in the down regulation of both oncoproteins avoiding the need to separately design the siRNA for these sequence (Palanichamy et al., 2010, Mol. Cancer Ther. 9, 2114-2122). Additionally, the effect of TGS is long lasting and genetically inherited to daughter cells. This therapeutic approach of gene silencing could be further honed and made tumour specific by utilizing PLAP promoter/enhancer system to drive the expression of shRNA targeting the LCR of these E6/E7 onco-proteins.

In case of HPV, since both the oncogenes (E6/E7) are driven by a common enhancer and promoter, targeting of the enhancer with siRNA could cause a potent decrease in the expression of the oncogenes E6 and E7 leading to apoptosis of the malignant cells.

c-Myc is a cooperative oncogene and one of the central players in oncogenesis in many cancers. Altered c-Myc expression is often an early step in multistage transformation and one on which other mutations are based (Dang, 2012, Cell 149, 22-35). Therefore, there is an apparent addiction of cancer cells to de-regulated c-Myc, as proposed in 2008 by Weinstein. This Achilles heel offers a potential therapeutic window for cancer cells. c-Myc up regulation has been noted in most liquid and solid tumours with colon cancer forming one of the top hierarchies in c-Myc up regulation. ME1a1 binding site between P1 and P2 promoter of c-Myc is required for sustenance of transcriptionally active dual c-Myc promoters (Albert et al., 2001, J. Biol. Chem. 276, 20482-20490). Since the P2 promoter is associated with 75-90% of the c-Myc transcripts (Wierstra and Alves, 2008, Cancer Res. 99, 113-333), it serves as an ideal candidate for targeted therapy. We have previously demonstrated that siRNA against c-Myc could induce TGS in glioma cells, leading to increased cell death (Mehndiratta et al., 2011, Mol. Pharm. 8, 2302-2309).

The possibility of rendering cancer cells more sensitive to drugs or toxins by introducing "suicide genes" has two alternatives: toxin gene therapy, in which the genes for toxic products are transduced directly into tumour cells, and enzyme-activating prodrug therapy, in which the transgenes encode enzymes that activate specific prodrugs to create toxic metabolites. The latter approach is known as suicide gene therapy, gene-directed enzyme prodrug therapy (GD-EPT) (Bridgewater et al., 1995 Eur. J. Cancer Oxf. Engl. 1990 31A, 2362-2370; Marais et al., 1996, Cancer Res. 56, 4735-4742), virus-directed enzyme prodrug therapy (VD-EPT) (Huber et al., 1994, Ann. N. Y. Acad. Sci. 716, 104-114; discussion 140-143) or gene prodrug activation therapy (GPAT) (Eaton et al., 2001, Gene Ther. 8, 557-567), which could be utilized in isolation or combined with other strategies to make a significant impact on cancer treatment.

PLAP promoter is a type of tumour type specific promoter which was characterized by Deng et al in 1992 (Cancer Res. 52, 3378-3383). Most of the tumour specific promoters like alpha-fetoprotein, specific for hepatocellular carcinoma (HCC), are polymerase II driven (Peng et al., 2013, LoS ONE 8, e53072). Often, such tumour specific promoters are weak in nature (Qiao et al., 2002, Gene Ther. 9, 168-175). Full length PLAP promoter sequence spans from −512 bp to +24 that is about 536 bp long, but the region between −363 to −170 bp contains strong negative control elements (Deng et al., 1992b). Presence of this silencing region in the whole promoter leads to the decrease in promoter activity, therefore we selected the region between −170 and +24 bp. When we testified the promoter activity of this region, it has the necessary strength to drive a transgene specifically in variety of PLAP expressing tumour cell lines.

Placental Like Alkaline Phosphatase (PLAP) was one of the first proteins found to be ectopically expressed by cancer cells; leading to the concept that deregulation of embryonic genes plays a significant role in the cancer process (Fishman et al., 1968, Enzymologia 34, 317-321; Fishman et al., 1968, Nature 219, 697-699). PLAP or the Regan isoenzyme has been demonstrated in malignancies of the lung, testis, ovary, pancreas, colon, lymph tissue, kidney, stomach, and bladder. Placental-like alkaline phosphatase or GCAP or Nagao isoenzyme is most frequently expressed in germ cell tumours and in ovarian cancer and serves as a useful tumour marker in patients with those tumours (Loose et al., 1984, Am. J. Clin. Pathol. 82, 173-177). The highest level of elevation seems to comprise germ cell tumours of the testis (Nathanson and Fishman, 1971, Cancer 27, 1388-1397, Sasaki and Fishman, 1973, Cancer Res. 33, 3008-3018). In the case of seminomas, PLAP or PLAP like enzymes seem to be established as clinically useful tumour markers (Jeppsson et al., 1984, Int. J. Cancer J. Int. Cancer 34, 757-761; Lange et al., 1982, Cancer Res. 42, 3244-3247). As the assays cannot distinguish between the closely related tumour markers GCAP and PLAP and there is only 12 amino acid substitution between the two proteins, so from last 30 years PLAP is generally used as a tumour marker. (Szentirmay et al., 1982, Cancer Detect. Prev. 5, 185-194.), suggested that PLAP could also be an oncodevelopmental marker of human gastric neoplasia.

Placental Like Alkaline Phosphatase (PLAP) also known as Germ Cell Alkaline Phosphatase (GCAP) is a marker of cancers of the ovary, testis, lung, and the gastrointestinal tract. GCAP is a useful immune-histochemical marker of carcinoma in situ of the testis. Elevated levels of PLAP or PLAP-like alkaline phosphatases have been demonstrated for a number of different malignancies including those from pancreas (in 27-30% cases), lung (9-40%), breast (5-23%), colon (10-54%), lymph nodes, kidney, stomach (36%) and bladder. (Jeppsson et al., 1984, Int. J. Cancer 34, 757-761; Lange et al., 1982, Cancer Res. 42, 3244-3247)

PLAP is ectopically expressed in wide range of tumors and consequently its promoter is active only in such neoplastic transformations with little or no activity in normal/ untransformed cells, so this promoter can be utilized for generating various tumour specific therapeutic modalities. (Milin, Jos Luis 1992, In Book entitled: Mammalian Alkaline Phosphatases, From Biology to Applications in Medicine and Biotechnology).

U.S. Pat. No. 6,867,036 relates to a nucleic acid construct which provides cell type-specific expression of a therapeutic transgene. In one embodiment, the amplification promoter element is a heat shock response element (HSE) and the transcription activator is HSF-1. The construct enables functional targeting of a therapeutic gene while avoiding undesirable effects in non-targeted cells, by combining sufficiently high-level expression to promote a desirable therapeutic outcome with exceptional tissue specificity. A series of promoter elements, constructs, vectors, and therapeutic approaches is presented for gene therapy of tumours such as melanoma and other genetic diseases.

U.S. Pat. No. 20110053861 relates to siRNA nucleic acid molecules that inhibit NF-kappaB expression and also methods of using the nucleic acid molecules.

U.S. Pat. No. 20110135620 relates to novel protein engineering strategy by combining the domains of two independent proteins into a molecular switch. The invention features polypeptides comprising a pro-drug activating enzyme and a protein that binds a cancer specific marker, polynucleotides encoding the polypeptides, and molecular switches for converting a pro-drug into a toxin, comprising the polypeptides. The invention also features methods for converting a pro-drug into a toxin, methods for treating cancer, and methods for making the molecular switches as well as kits.

U.S. Pat. No. 7,550,496 relates to hypoxia-activated pro-drugs can be used to treat cancer when administered alone or in combination with one or more anti-neoplastic agents.

U.S. Pat. No. 7,091,040 relates to a form of cancer therapy which exploits the cytotoxic properties of acetaminophen when converted to NABQI by the metabolic activity of tumour cell specific P450; vectors for use in the delivery of P450 to tumour cells; and therapeutic compositions comprising said vectors.

U.S. Pat. No. 20060099188 relates to DNA having tumor-specific transcription activity for use in the suicide gene therapy that combines the use of a gene for a drug metabolizing enzyme and a pro-drug for cancer therapy.

U.S. Pat. No. 7,321,030 relates to a promoter domain in the upstream side of exon 1B of IAI.3B gene has a specifically high promoter activity in ovarian cancer cells. An adenovirus having this promoter domain inserted in the E1 domain thereof exhibits a specifically high cell proliferation inhibitory effect on ovarian cancer cells. Thus, it is efficacious in gene therapy for ovarian cancer.

The majority of current therapeutic agents for cancer, in both cytotoxic and non cytotoxic categories, are chemicals foreign to the human body. Since most of these agents were designed by humans, not the nature, they have very high chances to bind to and interact with other cellular factors than their expected targets in the body. These "off-target" bindings and interactions account for significant opportunities for side effects. Radiation therapy causes severe epithelial damage leading to local necrosis. It can also cause radiation cystitis, sterility, hair loss, and fibrosis and generalized fatigue. Since radiation causes DNA damage it might cause secondary tumors also. Whatever be the therapy employed the greatest limitation of all the currently available cancer therapeutics is the inability to differentiate between normal and neoplastic cells.

The problem with the currently available cancer therapies is the lack of specificity of the same towards cancer cells, thus gives up rise to toxicity. Till now there has not been a efficient therapy which is able to combat wide range of tumours and induce cytotoxicity in neoplastically transformed cells only and spare the normal or untransformed cells.

SUMMARY OF THE INVENTION

Accordingly the main embodiment of the present invention provides a nucleic acid fusion construct comprising SEQ ID NO: 1 and at least one tumor specific enhancer response element.

Another embodiment of the present invention provides a nucleic acid construct as herein described in the present invention wherein the tumor specific enhancer response element for enhancers are selected from but not limited to NFκB enhancer, Hypoxia inducible factor (HIF), prostate specific antigen enhancer, simian 40 enhancer, cytomegalovirus enhancer or artificial enhancers.

Another embodiment of the present invention provides a nucleic acid construct as herein described in the present invention wherein the SEQ ID No.: 1 is placed in tandem with the said tumor specific enhancer response element.

Another embodiment of the present invention provides a nucleic acid construct as herein described in the present invention wherein nucleic acid fusion construct consist of multiple repeats of tumor enhancer response element.

Another embodiment of the present invention provides a nucleic acid construct as herein described in the present invention, wherein the tumor specific enhancer response element selected is NFκB enhancer.

Another embodiment of the present invention provides a nucleic acid construct as herein described in the present invention wherein the SEQ ID NO: 1 is placed in tandem with NFκB enhancer.

Another embodiment of the present invention provides a nucleic acid construct as herein described in the present invention wherein NFκB enhancer consists of multiple repeats. Another embodiment of the present invention provides a nucleic acid construct as herein described in the present invention wherein the fusion construct is capable of delivering and expressing cancer, neoplastic and tumor cells or tissues specific therapeutic agents.

Another embodiment of the present invention provides a nucleic acid construct as herein described in the present invention wherein the tumor, cancer or neoplastic cell or tissue specific therapeutic agents are selected from proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent.

Another embodiment of the present invention provides a nucleic acid construct as herein described in the present invention wherein the nucleic acid fusion construct is useful for cancer cell targeted gene therapy, gene dependent therapy, gene dependent enzyme therapy and gene dependent enzyme pro-drug therapy (GDEPT).

Another embodiment of the present invention provides a PLAP promoter having SEQ ID No. 1 as herein described in the present invention useful for cancer cell targeted gene therapy, gene dependent therapy, gene dependent enzyme therapy and gene dependent enzyme pro-drug therapy (GDEPT).

Another embodiment of the present invention provides a therapeutic agent capable of triggering gene/s capable of activating molecules or compounds or enzymes or peptides or proteins which convert pro-drug into a drug.

Another embodiment of the present invention provides a nucleic acid construct as herein described in the present invention wherein the fusion construct is capable of delivering and expressing cancer, neoplastic and tumor cells or tissues specific therapeutic agents.

Another embodiment of the present invention provides a nucleic acid construct as herein described in the present invention wherein the tumor, cancer or neoplastic cell or tissue specific therapeutic agents are selected from proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent.

Another embodiment of the present invention provides a nucleic acid construct as herein described in the present invention wherein the nucleic acid fusion construct is useful for cancer cell targeted gene therapy, gene dependent therapy, gene dependent enzyme therapy and gene dependent enzyme pro-drug therapy (GDEPT).

Another embodiment of the present invention provides a PLAP promoter having SEQ ID No. 1 as herein described in the present invention useful for cancer cell targeted gene therapy, gene dependent therapy, gene dependent enzyme therapy and gene dependent enzyme pro-drug therapy (GDEPT).

Another embodiment of the present invention provides a therapeutic agent capable of triggering gene/s capable of activating molecules or compounds or enzymes or peptides or proteins which convert pro-drug into a drug.

Yet another embodiment of the present invention provides a composition comprising a nucleic acid wherein the said nucleic acid sequence comprises of:
(a) A cell or tissue specific nucleic acid promoter having SEQ ID No. 1 or a nucleic acid fusion construct as claimed in claims 1-4, as originally filed;
(b) A therapeutic agent operably linked to a said cell or tissue specific nucleic acid promoter sequence or enhancer-promoter sequence.

In one embodiment the present invention provides a therapeutic agent delivery system comprising a composition as described herein in the present invention.

Another embodiment of the present invention provides a vector containing nucleic acid construct having SEQ ID No. 1 or a nucleic acid fusion construct as described in the present invention.

Another embodiment of the present invention provides a vector as described in the present invention wherein the nucleic acid construct or nucleic acid fusion construct is further linked to a therapeutic agent.

One embodiment of the present invention provides a method of preparing a tumor cell or tissue specific nucleic acid vector said method comprising the steps of:
(a) Isolating a cell or tissue specific promoter sequence having SEQ ID No. 1, optionally linking the SEQ ID No. 1 with a tumor specific enhancer response element sequence to obtain nucleic acid fusion construct;
(b) Inserting the promoter sequence or nucleic acid fusion construct of step (a) into a vector, and
(c) Obtaining a nucleic acid construct vector.

Another embodiment of the present invention provides a method as herein described wherein the tumor specific enhancer response element sequence is for enhancers selected but not limited to NFκB enhancer, Hypoxia inducible factor (HIF) or prostate specific enhancer.

Another embodiment of the present invention provides a method as described in the present invention wherein the SEQ ID No. 1 is placed in tandem with the said tumor specific enhancer response element.

Another embodiment of the present invention provides a pharmaceutical composition comprising, SEQ ID No. 1 or a fusion construct as as herein described in the present invention wherein the SEQ ID No. 1 or the fusion construct as herein described in the present invention is linked to a therapeutic agent along with a pharmaceutically acceptable carriers.

One embodiment of the present invention provides a method of treating or preventing cancer or tumor said method comprising administering to a subject a pharmaceutical composition as claimed described in the present invention.

One embodiment of the present invention provides a use of the composition as described in the present invention for the preparation of a medicament.

Another embodiment of the present invention provides the use of the composition as described in the present invention for treating or preventing cancer or tumor.

Another embodiment of the present invention provides the use of the composition as described in the present invention for inhibiting the growth, development or multiplication or spread of cancer, tumor or neoplastic cells.

One embodiment of the present invention provides a kit comprising a first and a second component:
  (a) wherein the first component comprises comprising, SEQ ID No. 1 or a fusion construct as described in the present invention, wherein the SEQ ID No. 1 or the fusion construct as described in the present invention are linked to a therapeutic agent; and
  (b) The second component a pro-drug.

Another embodiment of the present invention provides a kit as described in the present invention, wherein the therapeutic agent is molecule capable of activating the pro-drug of the second component.

In another aspect the present invention more specifically provides for tumor or cancer gene suiciding strategy using PLAP promoter or NFκB+PLAP promoter driven cytodeaminase (CD) expression for gene suiciding and this approach is called as PRADEPT i.e. promoter antibody dependent enzyme pro-drug therapy. This approach in the present invention provides for a broader application in combating wide range of tumors where PLAP is expressed.

BRIEF DESCRIPTION OF THE FIGURES

FIG. 1: PLAP promoter Sequence of interest which shows maximum activity yet retains tissue specificity FIG. 2: Enhancer Promoter system (Underlined sequences are the sequence of tetramer of NFκB DNA binding responsive elements) consists of a fusion chimera of NFκB responsive sequences and PLAP promoter

FIG. 5: Confirmation of promoter & enhancer-promoter based clones by restriction endonuclease digestion. (A) PLAP promoter spanning from −170 to +24 and cloned between Mlu1 and Nhe1 sites in MCS of PGL3 basic was confirmed by visualising a band of appropriate size by double digestion using respective restriction endonuclease enzymes. 1, 3, 7 represent clone numbers whereas M is the Marker. (B) Fusion construct comprising of tetramer of 10 bp long NFκB binding site and PLAP promoter cloned between Kpn1 and Nhe1 sites was verified by observing a band of required size by double digestion with mentioned restriction endonucleases. Lanes 1, 2, 3 and 4 represent respective enhancer+ promoter clones and M denotes marker.

FIG. 9: Effect of shRNA expressed by various TGS constructs on p53 target genes in SiHa. (A) Fall in the expression of E6 oncogene by various TGS inducing therapeutic modalities was accompanied by restoration of p53 as seen by increased expression of different p53 target genes by qPCR. The increase in expression of these genes depended on the strength of the therapeutic construct driving expression of shRNA similar to decrease in expression of E6. (B) Increase in the level of p53 at protein level after transfection with different therapeutic constructs was in consonance with the magnitude of the therapeutic construct governing shRNA expression. Thus, Transcriptional level results by qPCR were corroborated at the translation level by western blotting.

FIG. 10: Evaluating the influence on p53 and E2F1 targets by knockdown of E6 and E7 in CaSki. (A) Quantification of various p53 target genes by Real Time PCR after normalisation with three housekeeping genes (18s, GAPDH& β-actin) in CaSki after transfection with various TGS inducing shRNA constructs. There was an increase in the expression of PUMA and NOXA and it was in agreement with the strength of the construct driving shRNA expression. (B) The increase in level of p53 at translational level detected by western blotting was in consonance with the magnitude of therapeutic construct driving shRNA expression.

FIG. 11: Cell Survival in HPV-16 positive cervical cancer cell lines by various TGS inducing therapeutic constructs. Each cell clone was seeded onto a 6 well plate at a density of 50×103 cells/well. After overnight culture, cells were transfected with different plasmids in varied amounts ranging from 150 to 1200 ng/µl. Cell viability was determined by MTT assay 120 hours after transfection. Survival showed dependence both on the dose and the strength of the construct expressing shRNA. The data represent means of the cell viability, each performed in triplicate, and bars represent s.d.

FIG. 12: Cell apoptosis assayed in various in vitro models of HPV-16 (SiHa& CaSki) by Flow cytometry. Each cell clone was seeded onto a 25 cm2 flasks at density of 2×105 cells. After the cells were 50-60% confluent, they were transfected with 3 µg of various TGS based therapeutic modalities. 120 hours post transfection the percentage of cell apoptosis in each group was determined by flow cytometry. The degree of apoptosis was found to depend on the strength of the therapeutic construct expressing shRNA.

FIG. 13: Elucidating the mechanism of transcriptional gene silencing: (A) SiHa cells untreated or treated with TSA were transfected with NFκB+PLAP enhancer-promoter chimera expressing test & scrambled shRNA and harvested after 5 days. Chip was performed with antibodies against H3K9me2 and H3K27me3; antibodies against RNA polymerase and mouse IgG were respectively used as positive and negative controls for pull down. Input and immuno-precipitated DNA were measured by PCR with requisite primers and the enrichment at enhancer region was further quantified by qPCR. (B) Test shRNA does not cause DNA methylation. Bisulphite sequencing of targeted region showed no changes in test and control shRNA transfected SiHa.

FIG. 14: Amplification and Confirmation of various CD based prodrug activating constructs. (A) Coding sequence of yeast cytosine deaminase gene. (B) The coding sequence of FCY1 (yCD) (≈500 bp) was amplified with primers having incorporated Nco1 and Xba1 restriction sites. The amplified PCR products were eluted using Promega gel elution kit. (C) Coding cytosine deaminase region approximately 500 bp long cloned between Nco1 and Xba1 sites downstream to PLAP promoter, NFκB+PLAP enhancer-promoter system, SV40 promoter and promoter less system in PGL3-B/PGL3-C was confirmed by visualising a band of appropriate size in the respective clones by double digestion using Nco1 and Xba1 restriction endonucleases.

FIG. 15: CD expression at transcriptional and translational level by various gene suicide clones: Evaluating CD expression at transcriptional and translational level. Varied amounts of various GDEPT clones (SV40-CD, NFκB+PLAP CD, PLAP CD and Promoterless CD) were transfected in PLAP positive HeLa cell line and the expression of CD was assayed at mRNA level by real time PCR-(A) and at protein level by western blotting-(B). The expression was in accordance with the dose and the magnitude of therapeutic construct driving CD expression.

DETAILED DESCRIPTION OF THE INVENTION

Figure 3:
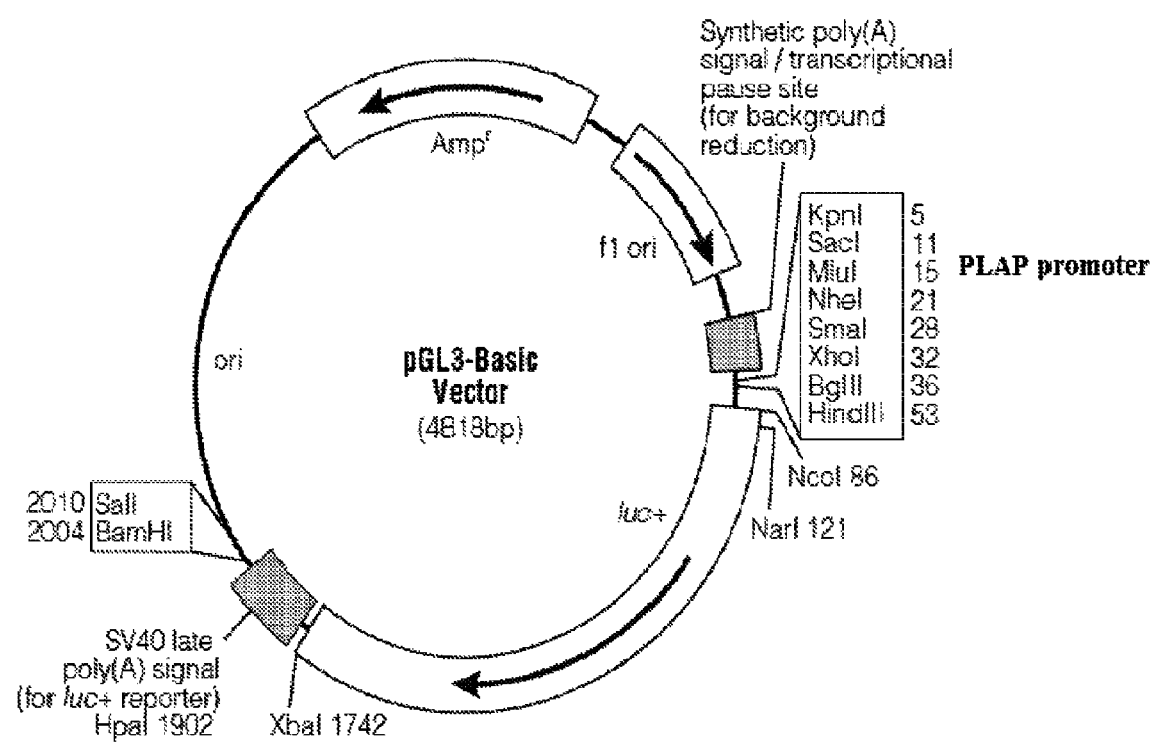
FIG. 3: Cloning strategy for PLAP promoter in promoter less luciferase expression vector pGL3 Basic: Schematic represantation of PLAP promoter spanning from −170 to +24 cloned between Mlu1 and Nhe1 sites in promoterless luciferase expression PGL3-Basic. Full length PLAP promoter was initially amplified with requiste primers in first round of PCR and in the second round of PCR the initial amplified and eluted PCR producted was used as template and amplified with primers having Mlu1 & Nhe1 restriction sites incorporated. The amplified PCR product was digested with the respective enzymes, eluted and ligated to the PGL3-Basic vector which was digested with same set of enzymes (Mlu1& Nhe1).

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The graphs, tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

Definitions

As used herein, the terms "Therapy/Therapies" when used in the context of the present invention refers to curing or healing or preventive remedy of diseased cells or tissues; and disease condition. In context of the present invention therapy also means the curing or healing or preventive remedy against the cancer, tumor or neoplastic cells. The therapy in the context of the present invention also means the use of System/s or Promoter System/s" Enhancer-Promoter System/s as described herein in the present invention for the curing or healing or preventive remedy caused by cancer or tumor; and cancer, tumor or neoplastic cells. In addition the therapy also means curing or healing or preventive remedy of cancer or tumor using System/s or Promoter System/s" Enhancer-Promoter System/s as described herein in the present invention.

As used herein, the terms "Cancer cells or neoplastic cells or tumor cells" when used in the context of the present invention refers to cells which cause cancer or tumor. These terms in context of the present invention have been used interchangeably.

As used herein, the terms "Normal cells or healthy cells" when used in the context of the present invention refers to cells which are normal having no cancer, tumor or neoplastic condition or state.

As used herein, the terms "Promoter System/s" when used in the context of the present invention refers to system/s or vector/s or construct/s which carry a PLAP promoter as described in the present invention capable of expressing in cancer, tumor or neoplastic cells. In the context of the present invention these terms also include systems that are capable of delivering and expressing therapeutic agents to cancer, tumor or neoplastic cells for the purpose of killing or eliminating the said cells. In context of the present invention said systems are able to deliver the therapeutic agents to such tumor, cancer or neoplastic cells which express PLAP promoter or capable of expressing PLAP promoter.

As used herein, the terms "Enhancer-Promoter System/s or Enhancer+PLAP" when used in the context of the present invention refers to system/s or vector/s or construct/s which carry the PLAP promoter linked to tumor specific enhancer response elements or tumor specific enhancers or tumor specific enhancer sequences as well.

As used herein, the term "tumor specific enhancer response element or tumor specific enhancer response element sequence" when used in the context of the present invention refers to sequences (wherein the sequences are selected from but are not limited to proteins sequences, peptides sequences, amino acid sequences, nucleotides sequences) which enables or are capable of facilitating binding of tumor specific enhancers to PLAP promoter sequence as described in the present invention. The tumor specific enhancer response element or tumor specific enhancer response element sequence as used in context of the present invention also includes tumor specific enhancers or tumor specific enhancer sequences as well. In context of the present invention the tumor specific enhancer or tumor specific enhancer response element includes but is not limited to NFκB tumor specific enhancer or NFκB tumor specific enhancer response element. In context of the present invention tumor specific enhancer response elements are such that they are capable of facilitating or enabling binding of tumor specific enhancers to PLAP promoter thereby augmenting or activating transcriptional expression of the PLAP promoter. The said systems are capable of expressing in cancer, tumor or neoplastic cells. In the context of the present invention the said terms also mean systems capable of delivering and expressing therapeutic agents to cancer, tumor or neoplastic cells for the purpose of killing or eliminating the said cells. In context of the present invention the enhancer-promoter system is selected from but not limited to NFκB+PLAP enhancer-promoter system.

As used herein, the terms "Therapeutic Agents or Therapeutic Molecules" when used in the context of the present invention refers to proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent. As used in the context of the present invention the therapeutic agents are also cytotoxic agents, which are used for the treatment of cancer or tumor. The cytotoxic agents used in the context of the present invention can be therapeutic agents or can be expressed as therapeutic agents which can be delivered and expressed in cancer, tumor or neoplastic cells using the promoter system or enhancer-promoter system as described in the present invention.

As used herein, the terms "prodrug activating molecules" when used in the context of the present invention refers to molecules or enzymes or proteins or peptides or nucleic acid sequences capable of activating genes which convert prodrug into a drug.

As used herein, the terms "Gene Therapy or Gene dependent therapy" when used in the context of the present invention refers to a therapy for expressing a therapeutic agents specifically inside transformed models to treat disease caused by cancer, tumor or neoplastic cells; or cancer or tumor.

As used herein, the term "subject" when used in the context of the present invention refers herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

As used herein, the terms "Gene suiciding therapeutic constructs" when used in the context of the present invention refers to tumour specific activation of pro-drug specifically inside neoplastic cells so as to lead to the cancer cell specific cytotoxicity.

A tumor cell over-expresses a particular protein because of increased specific transcriptional activity of tumor specific promoter. The present invention takes advantage of the aforesaid fact, wherein if a therapeutic agent is inserted downstream of this tumor specific promoter, then introduction of this therapeutic agent into these tumor cells allows specific expression of this therapeutic agent, thereby harming and killing the tumor cells only. In such kind of process the normal healthy cells or tissue that may also get transduced with recombinant construct would not express or express negligible levels of therapeutic agent or its product and express none in an ideal system. This methodology (transcriptional selectivity) not only enhances transfection efficiency, but also increases the expression of a therapeutic agent in tumor cells and simultaneously prevents or negligibly minimizes the expression of the therapeutic agent in normal and healthy (surrounding) cells.

Thus in one aspect the present invention provides a tumor cell specific promoter and/or enhancer-promoter system for delivering and expressing therapeutic agent. The present invention provides a unique identified PLAP promoter sequence region alone or in combination with a tumor specific enhancer response element sequence/region referred or with tumor specific enhancer. The enhancer response element enables/facilitates specific tumor specific enhancers to bind with PLAP promoter thereby enhancing or augmenting its transcriptional activity while retaining its specificity. The PLAP promoter sequence is in tandem with tumor enhancer response element sequence or tumor specific enhancer for driving therapeutic agent expression in a manner that is both specific and highly efficient.

The tumor enhancer response element sequences includes but not limited to any known sequence/s, artificial sequence/s, nuclear factor kappa-light-chain-enhancer of activated B cells (NFκB) sequence/s, Hypoxia inducible factor (HIF), simian virus 40 (SV40) enhancer, cytomegalovirus (CMV) enhancer and prostate specific antigen (PSA) enhancer.

PLAP Promoter

PLAP promoter is 536 base pairs long from −512 to +24 bases on chromosome 2 q34-q37 (Deng et al., 1992, Cancer Res. 52, 3378-3383). The sequences determined for the PLAP promoter in various cell lines between nucleotides −512 and +24 (with respect to the transcription start site) have 99% overall similarity to each other. Furthermore, they contain invariant TATA boxes (nucleotides −31 to −25) and Sp1 binding sites (nucleotides −84 to −76); an invariant set of four direct repeats (nucleotides −154 to −133) and two sets of invariant inverted repeats (first set, nucleotides −86 to −74 and −149 to −137; second set, nucleotides −280 to −272 and −294 to −286). The total conservation of these sequences suggests that they may play important roles in regulating transcription.

Nuclear factor-kappa B (NF-κB) (Ephrussi et al., 1985, Science 227, 134-140.) is a transcription factor, which is composed of five subunits (p50/p105, p52/p100, p65 (RelA), RelB and c-Rel) forming hetero or homodimers. NF-κB is normally retained in the cytoplasm as an inactive complex through the direct binding of the natural inhibitor of κB (IκB) (Karin, 1999). NF-κB can be activated by cytokines, UV radiation and reactive oxygen species (Karin, 1999, Oncogene 18, 6867-6874). A tumor can principally establish elevated NF-κB activity by intrinsic or extrinsic factors (Mantovani et al., 2008, Nature 454, 436-444). On one hand, enhanced NF-κB activity can be directly induced by mutations of NF-κB genes and/or oncogenes that activate the NF-κB signaling pathway. On the other hand, a tumor can achieve elevated NF-κB activity through increased cytokine release from the tumor microenvironment (Ben-Neriah and Karin, 2011). Finally, NF-κB can also contribute to tumor progression by controlling vascularization of tumors via up regulation of VEGF (vascular endothelial growth factor) and its receptors (Xie et al., 2010, Oncol. Rep. 23, 725-732). Thus, NF-κB which demonstrates enhanced activity in cancer cells can be tailored with tumour specific promoter to augment their activity. In a reporter vector, the enhancing activity of NF-kB can be further improved by employing its multiple tandem copies upstream of a less active promoter sequence.

In one aspect of the present invention provides the use of unique PLAP promoter sequence for enhancing the expression of therapeutic agents in cancer cells. In one aspect the present invention provides a region of PLAP promoter sufficient to drive tumor cell specific expression.

In one aspect the present invention provides for a unique PLAP promoter system alone or in combination with a tumor enhancer response element sequence or tumor specific enhancer which specifically expresses in those tumor cells which can express or are capable of expressing PLAP promoter only. The PLAP promoter system and/or Enhancer+PLAP system is such that it capable of delivering and expressing therapeutic agents to cancer, tumor or neoplastic cells which are capable of expressing PLAP promoter.

In another aspect as herein described in the present invention provides for a promoter or enhancer-promoter system for cell specific delivery and expression of therapeutic agents against lung, testicular, ovarian, cervical, colon, lymph tissue, kidney, stomach and bladder cancers.

One aspect of the present invention provides for a system for cancer cell targeted gene therapy, gene dependent therapy, gene dependent enzyme therapy and gene dependent enzyme pro-drug therapy (GDEPT). In another aspect, the present invention provides a system for triggering gene/s which is capable of activating molecules or compounds or enzymes or peptides or proteins which convert pro-drug into a drug.

In one aspect the present provides for a vector comprising construct of PLAP promoter system or fusion construct of enhancer-promoter system capable of delivering and expressing therapeutic agents to cancer, tumor or neoplastic cells or tissues. In one aspect the present invention provides for therapeutic agents which includes but not limited to proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent. The therapeutic agent as herein described in the present invention are the cytotoxic agents particularly the cancer, tumor or neoplastic cells or tissues. In one aspect of the present invention the therapeutic agents or cytotoxic agents described herein the present invention are capable of killing or eliminating the cancer, tumor or neoplastic cells or tissues. In one aspect of the present invention the therapeutic agents or cytotoxic agents described herein the present invention are capable of preventing the growth and multiplication of cancer, tumor or neoplastic cells or tissues. In one aspect the present invention also provides a system for delivery of therapeutic agents to cancer, tumor or neoplastic cells.

In one aspect of the present invention provides for tumor specific vehicular system using the novel PLAP promoter sequence alone or in combination with tumor enhancer response elements and process or method of developing such tumor specific vehicular system based on the promoter system and/or enhance-promoter system as herein described in the present invention.

In one aspect the present invention provides for a composition comprising a nucleic acid sequence of PLAP promoter system or enhancer-promoter system (particularly enhancer+PLAP promoter system) to which is linked a therapeutic agent. The system/s as herein described in the present invention enable or directs the expression of therapeutic agent to cancer, tumor or neoplastic cells or tissues.

One aspect of the present invention relates to a cancer, tumor or neoplastic specific therapeutic modality by using a region of the PLAP Promoter to drive the cancer, tumor or neoplasia specific expression of therapeutically useful agents. Thus the present invention provides for PLAP promoter (SEQ ID No. 1) and/or NFκB+PLAP enhancer-promoter system (SEQ ID No. 2) for a broader application in combating wide range of tumors where PLAP is expressed. Thus in one aspect of the present invention provides for an enhancer response element of NFκB enhancer.

In the present invention the NFκB+PLAP enhancer-promoter system works in manner such that PLAP promoter sequence is linked to unique artificial NFκB enhancer response elements, wherein the NFκB enhancer response elements facilitates or enables binding of NFκB enhancer with the PLAP promoter (thus referred herein throughout this invention as 'NFκB+PLAP enhancer-promoter system') thereby augmenting or activating the transcription activity of PLAP promoter for expression of tumor specific therapeutic agent. The NFκB+PLAP enhancer-promoter system fusion construct (SEQ ID No. 2) consists of multiple repeats of NFκB binding sites and PLAP promoter has been constructed to generate proof of the concept that PLAP promoter cloned in tandem with appropriate enhancers can achieve a greater therapeutic efficiency than the PLAP promoter alone.

In one aspect the present invention provides the hitherto unutilized novel cancer cell or tissue specific promoter system to combat wide range of tumors. More specifically the present invention provides to a method of tumor cell specific expression of therapeutic agents using PLAP promoter construct. In another aspect the present invention provides for the use of a region of the PLAP promoter in tandem with NFκB enhancer for driving gene expression in a manner that is both specific and highly efficient.

Thus, the present invention provides for PLAP promoter and/or NFκB+PLAP enhancer-promoter system for application in combating wide range of tumors selected from at least one of lung, testicular, ovarian, cervical, colon, lymph tissue, kidney, stomach and bladder cancers.

One aspect of the present invention provides for PLAP promoter system and/or NFκB+PLAP enhancer-promoter system for cancer cell targeted gene therapy, gene dependent therapy, gene silencing, gene suiciding, gene dependent enzyme therapy and gene dependent enzyme prodrug therapy (GDEPT). In another aspect the present invention provides a system for triggering gene/s capable of activating molecules or compounds or enzymes or peptides or proteins which convert pro-drug into a drug.

The present invention provides for a unique and unexpected utilization of PLAP promoter sequence alone or in combination with NFκB enhancer (NFκB+PLAP) based targeted gene expression in cancer or cancer cells. The PLAP and/or NFκB+PLAP system of the present invention is a very efficient in suppressing the cancer cells or gene silencing of cancer cells or gene suiciding of cancer cells. The specificity of the PLAP and/or NFκB+PLAP system of the present invention is such that it is not only specific but also highly efficient.

In another aspect the present invention provides for enhancing the targeted delivery of cancer therapeutics. More specifically the present invention provides for use of PLAP alone or in combination with NFκB enhancer system/s for such targeted delivery of cancer therapeutics that only eliminates or is toxic to the diseased cancer cells without effecting or disturbing the normal and healthy cells. Thus in one aspect the present invention provides for a system as described in the present invention which enables differentiation between the normal or healthy cells with neoplastic cells, thereby drastically reducing or eliminating the unwanted side effects which arise due to use of cancer therapeutics or cancer chemotherapy or cancer gene therapy.

The unique advantage of the present invention comes due to combination of PLAP promoter which is tissue specific more particularly cancer cell specific with an efficient a tetramer of 10 bp enhancer response element sequence of nuclear factor kappa-light-chain-enhancer of activated B cells (NFκB enhancer) (SEQ ID No. 2). It is has been found in the present invention that this combination system provides for strong and cancer/tumor cell specific expression. Particularly this expression system provides for strong and cancer/tumor/neoplastic cell specific transcriptional activity. Thus, this PLAP promoter and/or NFκB+PLAP enhancer-promoter system can be efficiently used for also driving various cancer gene therapy/ies. The PLAP promoter and/or NFκB+PLAP enhancer-promoter system of the present invention has highly cancer specific cytotoxicity. Thus the decrease in cell survival by tissue specific enhancer-promoter based therapeutic modality of NFκB+PLAP enhancer-promoter system as described in the present invention has been found to be highly efficient.

Thus, the one aspect the present invention also provides for tumor specific vehicular system using the novel PLAP promoter sequence alone and/or NFκB+PLAP enhancer-promoter system.

The uniqueness of aforementioned system is such that there is no significant cytotoxicity in non-PLAP cells or normal cells. This significantly demonstrates the cell, tissue and/or organ specific delivery of PLAP based vehicular system as described in the present invention.

In one aspect the present invention also provides for use and application of PLAP promoter alone or in combination with enhancer response elements or enhancer as described in the present invention for in-vitro and/or in-vivo ectopic expression in wide variety of cells, cell lines, or tissues. In another aspect the present invention provides for in-vitro and/or in-vivo ectopic transcription gene expression of PLAP promoter alone or in combination with enhancer response elements or enhancer as described in the present invention in wide variety of cells, cell lines, or tissues. In another aspect the present invention cells, cell lines or tissues selected for the ectopic expression or ectopic transcription gene expression of PLAP promoter alone or in combination with enhancer response elements or enhancer as described in the present invention are selected from but is not limited to stem cells, germ cells, cancer cells, tumor cells, neoplastic cells; or the cell lines of stem germ cells, cancer cells, tumor cells, neoplastic cells.

In another aspect the present invention provides for use and application of PLAP promoter alone or in combination with enhancer response elements or enhancer as described in the present invention for in-vitro and/or in-vivo ectopic expression and/or delivery of therapeutic agents and/or diagnostic agents in wide variety of cells, cell lines, or tissues.

In another aspect the present invention provides for use and application of PLAP promoter alone or in combination with enhancer response elements or enhancer as described in the present invention for in-vitro and/or in-vivo for expression and/or delivery of therapeutic agents and/or diagnostic agents in wide variety of cells, cell lines, or tissues.

In one aspect the present invention also provides for a composition or pharmaceutical composition comprising nucleic acid sequence of PLAP promoter sequence alone or in combination with a tumour enhancer promoting element as described in the present invention. The pharmaceutical composition of the present invention is intended for parenteral and oral administration. Preferably, the pharmaceutical composition described as herein in the present invention can be administered parenterally for example, intravenously, subcutaneously, intradermally or intramuscularly. The present invention also provides for agents which function as "pharmaceutically acceptable carrier or pharmaceutically acceptable excipient", wherein the term "pharmaceutically acceptable excipient or pharmaceutically acceptable excipient" means a pharmaceutically acceptable excipient or carrier, solution or additive to enable the delivery, dissolution or suspension of the pharmaceutical active ingredient as herein as described in the present invention. The pharmaceutical composition of the present invention may also contain pharmaceutically accepted auxiliary substances as required to approximate physiological conditions, such as pH adjusting and buffering agents, tonicity adjusting agents, wetting agents and the like. The pharmaceutical composition of the present invention may also contain pharmaceutically acceptable carriers, for example adjuvants, etc. The pharmaceutical composition of the present invention may also comprise of uricase conjugated with polymer or biopolymer, wherein the polymers can be common or commercially known or used polymers particularly pharmaceutical administered compositions, for e.g. PEG or its derivatives, dextran etc. The pharmaceutical compositions of this invention may also be administered in any convenient form, for example tablet, capsule, injection, granule or powder form.

The present invention also provides a method of treating, preventing and/or slowing the progression of cancer, tumor or neoplastic cells. Another aspect of the present invention provides for a method of treating, preventing and/or slowing the progression of cancer or tumor or neoplastic condition. In aspect the present invention provides for inhibiting growth and development cancer, tumor or neoplastic cells or tissues which are capable of expressing PLAP promoter or wherein PLAP promoter can be expressed alone or in combination with tumor specific enhancer or tumor specific response elements. The present invention also provides for method of treating, preventing or slowing the progression of cancer or tumor disease or disorder caused by cancer, tumor or neoplastic cells by administering a pharmaceutical composition as described in the present invention.

In one aspect the present invention provides use of PLAP promoter alone or in combination with enhancer response elements or enhancer response element sequences or enhancer/s or enhancer/s sequences for expression in stem cells or germ cells. In one aspect the present invention provides use of PLAP promoter alone or in combination with enhancer response elements or enhancer response element sequences or enhancer/s or enhancer/s sequences for expression and/or delivery of therapeutic agents to germ cells or stem cells. In one aspect the present invention provides use of PLAP promoter alone or in combination with enhancer response elements or enhancer response element sequences or enhancer/s or enhancer/s sequences for expression and/or delivery of any agent/s to germ cells or stem cells which enable growth, development or differentiation of the germ cells or stem cells.

Accordingly the main embodiment of the present invention provides a nucleic acid fusion construct comprising SEQ ID NO: 1 and at least one tumor specific enhancer response element.

Another embodiment of the present invention provides a nucleic acid fusion constrict comprising SEQ ID No. 1 and at least one tumor specific enhancer.

Another embodiment of the present invention provides for a nucleic acid fusion constrict comprising SEQ ID No. 1, wherein the tumor specific enhancer response element is facilitates or enables binding of tumor specific enhancer to the Sequence ID No. 1.

Another embodiment of the present invention provides for a PLAP promoter having SEQ ID No. 1 and at least one tumor specific enhancer response element.

Another embodiment of the present invention provides for a PLAP promoter having SEQ ID No. 1 and at least one tumor specific enhancer.

Another embodiment of the present invention provides a nucleic acid construct as herein described in the present invention wherein the tumor specific enhancer response element for enhancers are selected from but not limited to NFκB enhancer, Hypoxia inducible factor (HIF), prostate specific antigen enhancer, simian 40 enhancer, cytomegalovirus enhancer or artificial enhancers.

Another embodiment of the present invention provides a nucleic acid construct as herein described in the present invention wherein the SEQ ID No.: 1 is placed in tandem with the said tumor specific enhancer response element.

Another embodiment of the present invention provides a nucleic acid construct as herein described in the present invention wherein nucleic acid fusion construct consist of multiple repeats of tumor enhancer response element.

Another embodiment of the present invention provides a nucleic acid construct as herein described in the present invention, wherein the tumor specific enhancer response element selected is NFκB enhancer.

Another embodiment of the present invention provides a nucleic acid construct as herein described in the present invention wherein the SEQ ID NO: 1 is placed in tandem with NFκB enhancer.

Another embodiment of the present invention provides a nucleic acid construct as herein described in the present invention wherein NFκB enhancer consists of multiple repeats.

Another embodiment of the present invention provides a nucleic acid construct as herein described in the present invention wherein the SEQ ID No. 1 is a unique PLAP promoter sequence.

Another embodiment of the present invention provides a nucleic acid construct as herein described in the present invention wherein the fusion construct is capable of delivering and expressing cancer, neoplastic and tumor cells or tissues specific therapeutic agents.

Another embodiment of the present invention provides a nucleic acid construct as herein described in the present invention wherein the tumor, cancer or neoplastic cell or tissue specific therapeutic agents are selected from proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent.

Another embodiment of the present invention provides a nucleic acid construct as herein described in the present invention wherein the nucleic acid fusion construct is useful for cancer cell targeted gene therapy, gene dependent therapy, gene dependent enzyme therapy and gene dependent enzyme pro-drug therapy (GDEPT).

Another embodiment of the present invention provides a PLAP promoter having SEQ ID No. 1 as herein described in the present invention useful for cancer cell targeted gene therapy, gene dependent therapy, gene dependent enzyme therapy and gene dependent enzyme pro-drug therapy (GDEPT).

Another embodiment of the present invention provides a therapeutic agent capable of triggering gene/s capable of activating molecules or compounds or enzymes or peptides or proteins which convert pro-drug into a drug.

Another embodiment of the present invention provides a nucleic acid construct as herein described in the present invention, wherein the therapeutic agents selected but are not limited to FCY1 gene, cytosine deaminase and small hairpin RNA (shRNA).

Another embodiment of the present invention provides a nucleic acid construct as herein described in the present invention wherein the said nucleic acid fusion construct comprises a small hairpin RNA (shRNA) capable of targeting the promoter of c-myc.

Another embodiment of the present invention provides a nucleic acid construct as herein described in the present invention for use in delivering and expression of tumor, cancer or neoplastic cell or tissue specific therapeutic agents are proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, prodrug activating molecules, a dye, pro-apoptotic agent, apoptotic agent.

Yet another embodiment of the present invention provides a composition comprising a nucleic acid wherein the said nucleic acid sequence comprises of:
  (a) A cell or tissue specific nucleic acid promoter having SEQ ID No. 1 or a nucleic acid fusion construct as claimed in claims 1-4, as originally filed;
  (b) A therapeutic agent operably linked to a said cell or tissue specific nucleic acid promoter sequence or enhancer-promoter sequence.

Another embodiment of the present invention provides a composition as herein described in the present invention wherein the therapeutic agent is selected proteins, peptides, nucleotides, genes, gene sequences, nucleotides, antibodies, anticancer agent, cancer therapeutic agent, antibody fragments, drugs, toxins, enzymes, nucleases, hormones, immunomodulators, antisense oligonucleotides, small-interfering RNA (si-RNA), aptamers, chelators, radiotherapy compounds, diagnostic agents, chemotherapy agents, imaging agents, cytokines, chemokine, pro-drug activating molecules, a dye, pro-apoptotic agent, apoptotic agent.

Another embodiment of the present invention provides a composition as herein described in the present invention, wherein the therapeutic agent is a cytotoxic agent.

Another embodiment of the present invention provides a composition as herein described in the present invention, wherein the nucleic acid fusion construct comprises of SEQ ID No. 2.

One embodiment of the present invention provide a method of inhibiting or preventing or slowing down the growth of a cancer, tumor or neoplastic cell or tissue said method comprising administering to a subject a composition as claimed in claim 15, as originally filed, along with a pharmaceutically acceptable carrier.

In one embodiment the present invention provides a therapeutic agent delivery system comprising a composition as described herein in the present invention.

Another embodiment of the present invention provides a vector containing nucleic acid construct having SEQ ID No. 1 or a nucleic acid fusion construct as described in the present invention.

Another embodiment of the present invention provides a vector as described in the present invention wherein the nucleic acid construct or nucleic acid fusion construct is further linked to a therapeutic agent.

Another embodiment of the present invention provides a vector as described in the present invention wherein the vector is capable of delivering and expressing in cancer, neoplastic and/or tumor cells or tissues.

One embodiment of the present invention provides a method of preparing a tumor cell or tissue specific nucleic acid vector said method comprising the steps of:
  (a) Isolating a cell or tissue specific promoter sequence having SEQ ID No. 1, optionally linking the SEQ ID No. 1 with a tumor specific enhancer response element sequence to obtain nucleic acid fusion construct;
  (b) Inserting the promoter sequence or nucleic acid fusion construct of step (a) into a vector; and
  (c) Obtaining a nucleic acid construct vector.

Another embodiment of the present invention provides a method as herein described wherein the tumor specific enhancer response element sequence is for enhancers selected but not limited to NFκB enhancer, Hypoxia inducible factor (HIF) or prostate specific enhancer.

Another embodiment of the present invention provides a method as described in the present invention wherein the SEQ ID No. 1 is placed in tandem with the said tumor specific enhancer response element.

Another embodiment of the present invention provides a method as described in the present invention wherein tumor specific enhancer response element is present in multiple repeats.

Another embodiment of the present invention provides a method as described in the present invention wherein the nucleic acid fusion construct is having SEQ ID No. 2.

Another embodiment of the present invention provides a pharmaceutical composition comprising, SEQ ID No. 1 or a fusion construct as herein described in the present invention wherein the SEQ ID No. 1 or the fusion construct as herein described in the present invention is linked to a therapeutic agent along with a pharmaceutically acceptable carriers.

One embodiment of the present invention provides a method of treating or preventing cancer or tumor said method comprising administering to a subject a pharmaceutical composition as claimed described in the present invention.

One embodiment of the present invention provides a use of the composition as described in the present invention for the preparation of a medicament.

Another embodiment of the present invention provides the use of the composition as described in the present invention for treating or preventing cancer or tumor.

Another embodiment of the present invention provides the use of the composition as described in the present invention for inhibiting the growth, development or multiplication or spread of cancer, tumor or neoplastic cells.

One embodiment of the present invention provides a kit comprising a first and a second component:
(a) wherein the first component comprises comprising, SEQ ID No. 1 or a fusion construct as described in the present invention, wherein the SEQ ID No. 1 or the fusion construct as described in the present invention are linked to a therapeutic agent; and
(b) The second component a pro-drug.

Another embodiment of the present invention provides a kit as described in the present invention, wherein the therapeutic agent is molecule capable of activating the pro-drug of the second component.

In another embodiment the present invention provides for use of and application of PLAP promoter alone or in combination with enhancer response elements or enhancer as described in the present invention for in-vitro and/or in-vivo ectopic expression in wide variety of cells, cell lines, or tissues.

In another embodiment the present invention provides for use of and application of PLAP promoter alone or in combination with enhancer response elements or enhancer as described in the present invention for in-vitro and/or in-vivo ectopic transcription gene expression in wide variety of cells, cell lines, or tissues.

In another embodiment the present invention provides for use of and application of PLAP promoter alone or in combination with enhancer response elements or enhancer as described in the present invention for in-vitro and/or in-vivo ectopic expression and/or delivery of therapeutic agents and/or diagnostic agents in wide variety of cells, cell lines, or tissues.

In another embodiment the present invention provides for use of and application of PLAP promoter alone or in combination with enhancer response elements or enhancer as described in the present invention for in-vitro and/or in-vivo ectopic transcription gene expression for expression and/or delivery of therapeutic agents and/or diagnostic agents in wide variety of cells, cell lines, or tissues.

In another embodiment the present invention provides for use and application of PLAP promoter alone or in combination with enhancer response elements or enhancer as described in the present invention wherein the cells, cell lines, or tissues are selected from but not limited to stem cells, germ cells, cancer cells, tumor cells, and neoplastic cells; or the cell lines of stem germ cells, cancer cells, tumor cells, and neoplastic cells.

In another aspect the present invention more specifically provides for tumor or cancer gene suiciding strategy using PLAP promoter or NFκB+PLAP promoter driven cytodeaminase (CD) expression for gene suiciding and this approach is called as PRADEPT i.e. promoter antibody dependent enzyme pro-drug therapy. This approach in the present invention provides for a broader application in combating wide range of tumors where PLAP is expressed.

In the present invention a region of PLAP promoter has been identified which is sufficient to drive tumour specific expression. Also to enhance the tumour specific promoter driven expression, while retaining the specificity of expression a fusion construct comprising of multiple repeats of NFκB binding sites and PLAP promoter was generated. The promoter/promoter-enhancer activities were assayed by various reporter systems in a battery of cell lines along with their appropriate controls. The utility of these constructs for gene dependent enzyme prodrug therapy (GDEPT) has been demonstrated and results reveal the activation of the inactive form of drug 5-fluorocytosine to its active form 5-fluorouracil by the enzyme cytosine deaminase when its expression was governed by PLAP promoter/enhancer systems. The promoter/promoter-enhancer systems were also evaluated for their expression of shRNA's targeting the P2 promoter of c-myc oncogenes well as the common LCR of HPV-16 E6/E7 oncoproteins via transcriptional gene silencing (TGS).

The PLAP promoter/enhancer driven expression of shRNA would impart the tumour specificity to these potent gene silencing sequences causing TGS and hence could be used for the treatment of cancer in future. The utility of PLAP promoter/enhancer systems for GDEPT offers another avenue of harnessing this tumour specific promoter/enhancer system for cancer therapy.

PLAP is being ectopically expressed in wide range of tumours, so its promoter which is active only in such malignant conditions with little or no basal level activity in normal cells was used to drive the expression of shRNA targeting the c-myc oncogene in colon cancer and E6/E7 oncoproteins of HPV-16 in cervical cancer. PLAP promoter/enhancer systems is also being utilized for the activation of the prodrug 5-Fluorocytosine to 5-fluorouracil.

The identified region of PLAP promoter is sufficient to drive tumour specific expression. Also to enhance the tumour specific promoter driven expression, while retaining the specificity of expression a fusion construct comprising of multiple repeats of NFκB binding sites and PLAP promoter was generated. Thus, the novel features of the invention include the identification of the tumour specific region of PLAP promoter and the generation of tumour specific promoter enhancer system comprising of tetramer of NFκB and PLAP promoter The identification of the tumour specific region of the PLAP promoter can pave the way for the generation of various tumour specific therapeutic modalities which can overcome the drawbacks associated with the current cancer therapies.

Activity of PLAP promoter is limited to tumor micro environment. So it can be utilized to generate various tumor specific therapeutic modalities. In present studies it has been found that it can induce gene silencing & gene suiciding across wide range of tumors highlighting its potential to be used as therapeutic modality. Silencing of oncogenes with high degree of tumor specificity would translate into products which have a relevance to tumor therapy both as unimodal applications as well as in synergy with conventional or pathway specific therapy.

The following description is of exemplary embodiments only and is not intended to limit the scope, applicability or configuration to the invention in any way, Rather, the following description provides a convenient illustration for implementing exemplary embodiments of the invention various changes to the described embodiments may be made in the functions and arrangement of the elements described without departing from the scope of the invention.

EXAMPLES

Example 1

Cell Culture:
PLAP positive cervical cancer cell lines (HeLa, SiHa and CaSki) and PLAP negative hepatoma cell line (HepG2) and non-PLAP, non-human cell line (CHO) were used in this study. SiHa, HeLa, HepG2 & CHO were maintained in DMEM whereas CaSki was maintained in RPMI 1640 with 10% FBS and 5% $CO_2$ at 37° C.

Example 2

Figure 4:
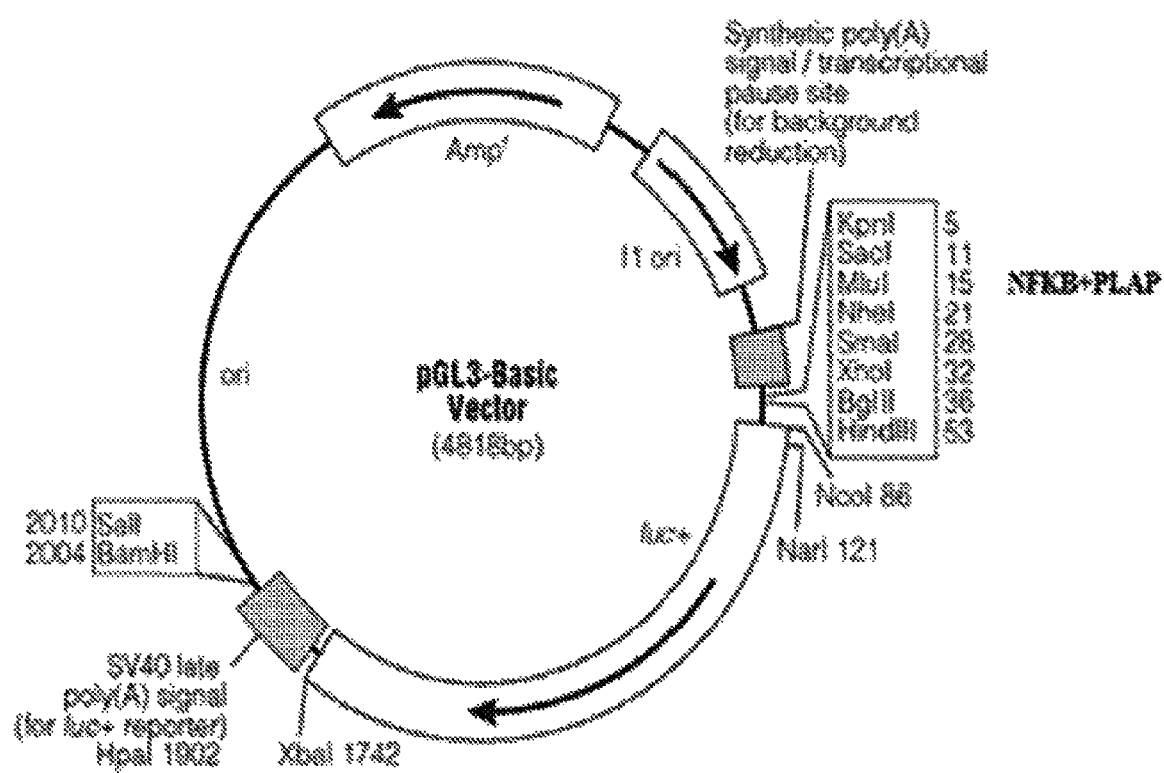
FIG. 4: Cloning strategy for NFκB+PLAP enhancer promoter chimera in promoter less luciferase expression vector pGL3 Basic: Schematic representation of tetramer of NFκB DNA responsive elements conjugated to PLAP promoter spanning from −170 to +24 & cloned between Kpn1 and Nhe1 sites in promoterless luciferase expression PGL3-Basic. 40 bp long NFκB DNA responsive element having Kpn1 & Mlu1 at 5' and 3' ends respectively was annealed and ligated to PLAP promoter already cloned in PGL3-Basic having Mlu1 & Nhe1 at 5' and 3' ends. Thus, the NFκB+PLAP enhancer-promoter system has Kpn1 and Nhe1 at 5' and 3' ends with 5'Mlu1 of promoter switched to 3'Mlu1 of NFκB enhancer.

Construction of Promoter/Enhancer Based Reporter Systems:

The human PLAP promoter sequence spanning from −170 to +24 relative to the transcription start site (TSS) was amplified from genomic DNA following a nested PCR strategy (FIG. 1). In the initial round of PCR 500 bp sequence spanning the 5' and 3' ends of the promoter region was amplified with requisite primers and in the second round the initial PCR product was used as template to amplify the desired promoter region (−170 to +24) with another set of primers having Mlu1 & Nhe1 restriction sites incorporated. The amplified PCR product was eluted and cloned between Mlu1 & Nhe1 in the MCS of promoter less luciferase expression vector pGL3 Basic (Promega). For generation of NFκB+PLAP enhancer-promoter system, a tetramer of NFκB DNA binding sites (GGGAATTTCC) having Kpn1 & Mlu1 at 5' and 3' ends respectively was annealed using annealing buffer (Tris HCl 10 mM, EDTA 100 mM, 1M NaCl) and cloned in a vector which already had PLAP promoter cloned between Mlu1 & Nhe1 sites. Thus, the enhancer-promoter system has Kpn1 and Nhe1 at 5' and 3' ends with 5'Mlu1 of promoter switched to 3'Mlu1 of NFκB enhancer (FIGS. 2-4).

Example 3

In Vitro Transfection and Reporter Gene Assays:

All transfections were performed using Lipofectamine™ 2000 transfection reagent according to manufacturer's instruction (Invitrogen). Briefly, ($1\times10^6$/well) cells were cultured in 6-well plates overnight. The luciferase reporter vectors (PLAP-luc, NFκB+PLAP−luc & pG13 Basic; 1 μg well$^{-1}$) were co-transfected in 20:1 ratio with Renilla luciferase expression vector (pRL-TK), an internal control for normalisation of the transcriptional activity of the reporter vectors. Forty-eight hours post transfection, the cells were lysed and luciferase activities were assayed using Dual Luciferase Assay reagents (Promega) according to manufacturer's protocol. All transfections were performed in triplicate and all experiments were repeated at least twice.

After accessing the activity of promoter/promoter enhancer system in a battery of neoplastically transformed cell lines along with their appropriate controls, it was found that the activity of PLAP promoter and NFκB+PLAP promoter enhancer systems was of optimum level only in carcinoma cell lines expressing PLAP with little or no activity in the control cell lines.

Next, this promoter/promoter enhancer system were utilized for driving the expression of shRNA targeting the p2 promoter of c-myc oncogene in colon cancer and the common LCR of E6/E7 oncogenes in HPV-16 integrated cervical carcinoma cell lines via TGS.

Full length PLAP promoter spans from −512 to +24 base pairs (Deng et al., 1992), but the region which shows maximum activity ranges from −170 to +24 base pairs. This region of the promoter was amplified requisite primers and cloned in promoter less luciferase expression vector PGL3 basic.

To augment the transcriptional activity of PLAP promoter while maintaining its cancer targeting specificity novel chimeric enhancer-promoter system was designed. To design this novel chimeric enhancer-promoter system novel artificial tumor specific enhancer response element sequences were prepared which comprised of tetramer of NFκB DNA binding sites (GGGAATTTCC) placed upstream to the basal PLAP promoter (NFκB+PLAP) (SEQ ID No. 2).

By restriction endonuclease digestion, it was authenticated that two target segments; PLAP promoter & NFKB+ PLAP promoter were inserted correctly into corresponding vectors respectively. The sequences of both inserted fragments in all the recombinant vectors were confirmed by sequencing from professional agencies and it was identical with earlier published data (FIG. 5).

Example 4

The Transcriptional Proficiency and Specificity Derived from Various Combinations of PLAP Promoter and Enhancer Systems in Various In Vitro Models.

The region of PLAP promoter spanning from −170 to +24 containing invariant TATA boxes (nucleotides −31 to −25) & Sp1 binding sites (nucleotides −84 to −76) cloned in promoter less luciferase expression vector PGL3 basic was transfected in battery of PLAP positive cell cervical cell lines (HeLa, SiHa and CaSki) and appropriate PLAP negative cell lines HepG2 (Hepatoma) & CHO. Promoter activity was assayed in these in vitro model systems by dual luciferase assay.

To develop an optimal enhancer-promoter system for improving the transcriptional activity of PLAP promoter a fusion construct comprising of PLAP promoter & tetramer of NFKB binding sites cloned in PGL3 basic was evaluated by dual luciferase assay in the above mentioned cell lines. Furthermore, we compared the transcriptional activity of PLAP promoter/enhancer systems with strong SV40 virus promoter (PGL3 C).

Figure 6:
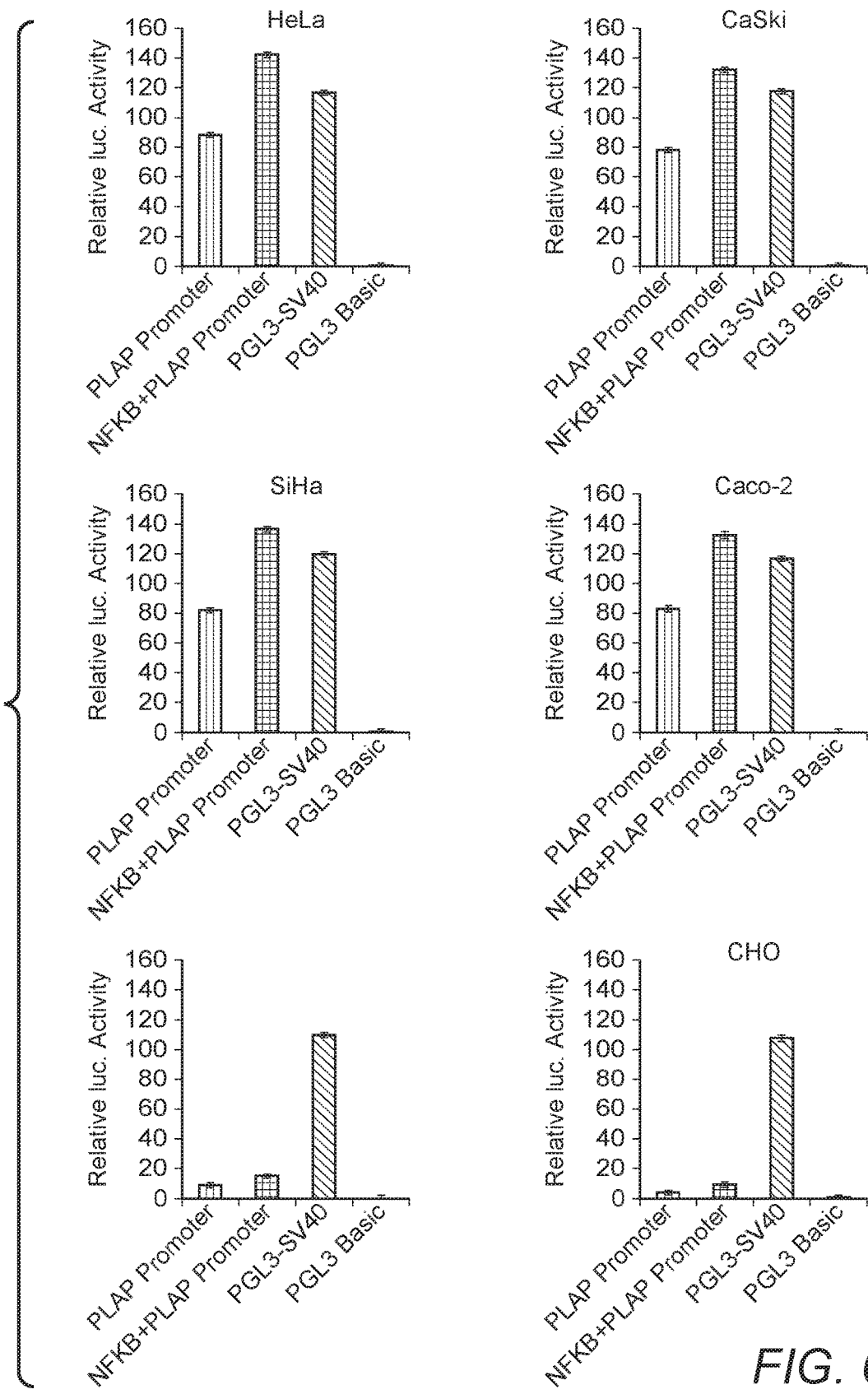
FIG. 6: The transcriptional activity and specificity of basal PLAP promoter in combination with NFκB in various cellular systems. (A) PLAP positive HPV-18 integrated cervical cancer cell line (HeLa), HPV-18 & HPV-16 integrated cell line (CaSki), HPV-16 integrated cell line (SiHa) and PLAP positive colon cancer cell line Caco-2, PLAP negative hepatoma cell lines (HepG2) & (CHO) were co-transfected separately in triplicates with luciferase expression vectors (PLAP-luc, NFκB+PLAP-luc & SV40-luc) and Renilla expression vector (pRL-TK). The luciferase activity of each transfection was normalised by the Renilla reading. The luciferase activity is represented by the ratio of specific promoter or enhancer promoter over the activity of PGL3-Basic. The column represents the mean of three measurements and the bar represents the s.d. PLAP promoter and NFκB+PLAP enhancer promoter chimera demonstrated tissue selective expression while as SV40 based luciferase system showed non-specific tissue expression. The generated constructs showed specific activity in concordance with their strength and the trend observed was NFκB−PLAP Pr>SV40 Pr>PLAP Pr. Y-axis represents the relative luciferase activity over pGL3-Basic and X-axis represents various luciferase expressing reporter constructs.
Figure 6:
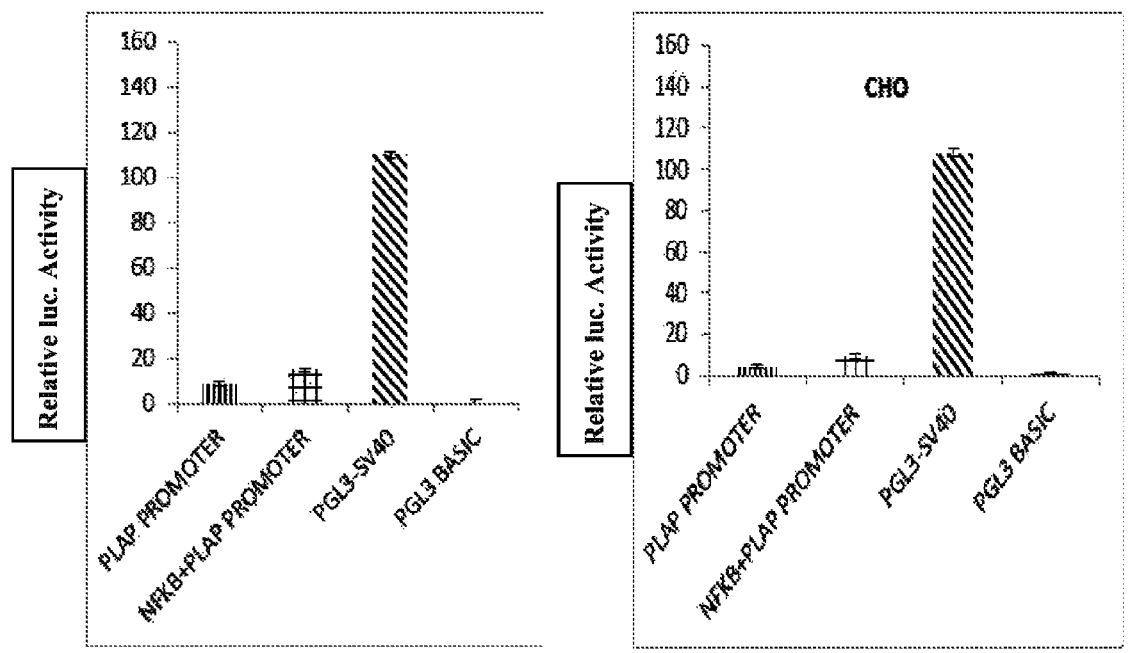

PLAP promoter and NFKB−PLAP enhancer-promoter system demonstrated selective transcriptional activity in all the PLAP positive cell lines but not in PLAP negative cell line. The transcriptional activity of NFKB−PLAP enhancer-promoter system was highly comparable to that of strong SV40 virus promoter in all PLAP positive cervical cancer cell lines. The SV40 promoter also demonstrated high transcriptional activity in PLAP negative hepatoma cell line HepG2 & CHO (FIG. 6).

Example 5

Design and Construction of shRNA Based Therapeutic Constructs:

ShRNA was designed from the screened and tested siRNA1 sequence targeting one of the NF-1 binding sites in the enhancer of HPV-16 using applied Bio science online shRNA designing tool. The sticky ends for BamH1 and Hind111 were pre added at 5' and 3' ends of the shRNA sequence. ShRNA oligos were annealed and cloned in shRNA expression vector pSilencer 4.1 (Ambion) between BamH1 and Hind111 sites.

To use enhancer/promoter system for shRNA expression both enhancer and promoter systems were modified by amplification separately only up to +2 sequence relative to TSS with primers having EcoR1 and BamH1 restriction sites incorporated using NFKB+PLAPenhancer-promoter and PLAP promoter pGL3 Basic plasmids as templates respectively.

The modified NFKB+PLAP enhancer-promoter system (mNFκB+PLAP) and PLAP promoter (mPLAP) were cloned separately in pSilencer 4.1 vector by replacing its CMV promoter with mNFKB+PLAPin case of enhancer-promoter system or mPLAP in case promoter system using EcoR1 and BamH1 restriction endonucleases. Similar strategy was followed for designing and cloning of negative control scrambled shRNA.

Transfection of TGS Inducing shRNA Therapeutic Modalities:

Cells were plated at $5 \times 10^4$ cells per well in a 24-well plate, $10^5$ cells per well in a six-well plate, $3 \times 10^5$ cells per 25 cm² flask, or $10^6$ cells per 75 cm2 flask. Twenty-four hours later, they were transfected with various TGS inducing therapeutic constructs (CMV-shRNA, NFκB+PLAP shRNA and PLAP shRNA) along with their scrambled shRNA clones using Lipofectamine™ 2000 (Invitrogen) and transfections were done as per the manufacturer's protocol.

These clones were transfected in cervical cancer cell lines SiHa & CaSki (HPV-16 integrated) and colon cancer cell line Caco-2 (elevated c-myc level), along with their appropriate controls. Post transfection, knock down studies were evaluated at both transcriptional level by Real time PCR & translational level by ECL.

Nested PCR strategy was followed to amplify yeast cytosine deaminase gene, FCY1 gene from yeast DNA. The amplified 500 bp long FCY1 with Incorporated restriction sites was cloned downstream to PLAP promoter/enhancer system. The clones were screened and confirmed by sequencing. The confirmed clones were transfected in PLAP+VE cancer cell lines along with their appropriate controls for cytosine deaminase assays as well as to evaluate the cytotoxicity effects produced by our prodrug activating machinery.

Example 6

Generation and Characterization of Various Tumour Specific Transcriptional Gene Silencing (TGS) Inducing Therapeutic Constructs:

Having established the strength and specificity of PLAP promoter and NFκB+PLAPenhancer-promoter cassettes by luciferase reporter assay system, we studied their efficacy for TGS. We already had in our laboratory the screened and tested siRNA (siRNA1) targeting the NF-1 binding sites in HPV-16 enhancer (Palinachamy et al, 2010). ShRNA was designed both from test siRNA sequence and its control scrambled sequence using online shRNA designing tool. Test ShRNA targeting the HPV-16 enhancer & its scrambled control shRNA were cloned downstream to PLAP promoter (PLAP ShRNA) as well as NFκB4+PLAP enhancer-promoter system (NFκB+PLAP shRNA) in shRNA expression vector pSilencer4.1.Test and control shRNA's were also cloned downstream to CMV promoter (CMV shRNA) in the mentioned shRNA expression system to compare the strength and specificity of the constructs.

Figure 7:
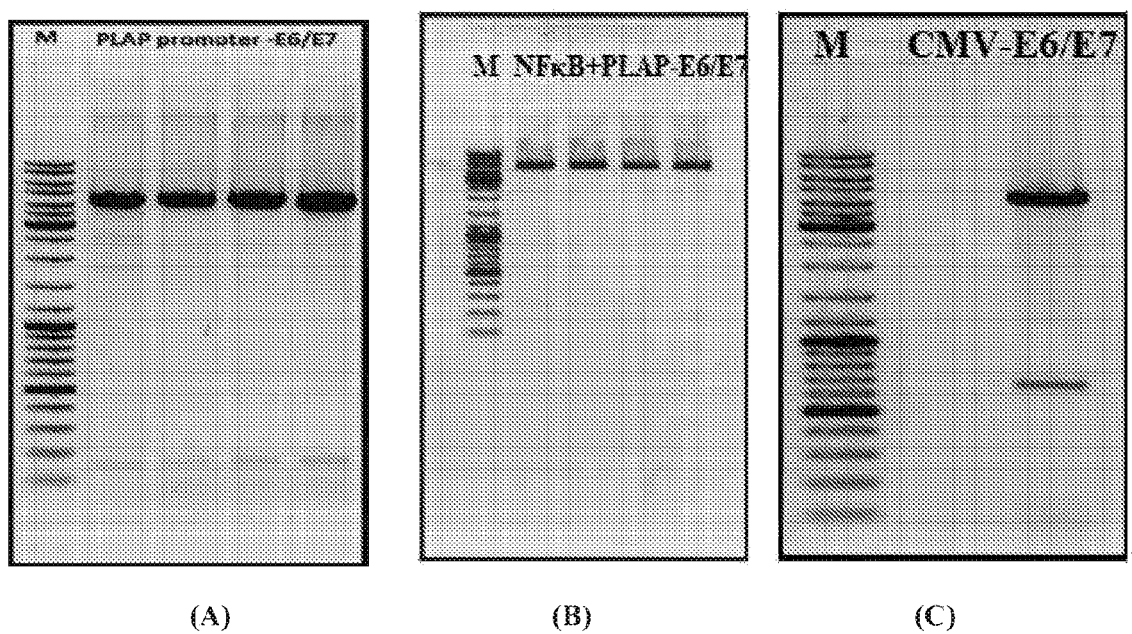
FIG. 7: Confirmation of various shRNA based TGS inducing therapeutic constructs by restriction endonuclease digestion. (A) PLAP promoter spanning from −170 to +2, cloned between EcoR1 & BamH1 and shRNA cloned between BamH1 & HindIII sites in polymerase II based shRNA vector pSilencer4.1 was confirmed by visualising a band of appropriate size by double digestion using EcoR1 & HindIII restriction endonuclease enzymes. (B) NFκB+PLAP enhancer-promoter chimera comprising of tetramer of 10 bp long NFκB binding site and PLAP promoter ranging from −170 to +2 cloned between EcoR1 & BamH1 and shRNA cloned between BamH1 & HindIII sites in pSilencer4.1 was verified by observing a band of required size by double digestion with EcoR1 & HindIII restriction endonucleases. (C) ShRNA cloned between BamH1 & HindIII sites downstream to CMV promoter was confirmed by double digestion with EcoR1 & HindIII releasing an insert of the length of CMV promoter+shRNA.

By restriction endonuclease digestion, it was authenticated that four target segments; PLAP promoter & NFKB+ PLAP enhancer-promoter, CMV promoter and shRNA were inserted correctly into shRNA vector pSilencer4.1 respectively. The sequences of all inserted fragments in all the recombinant vectors were confirmed by sequencing from professional agencies (FIG. 7).

Example 7

Attenuation in E6 and E7 Expression is Specific to HPV-16 & in Consonance with Magnitude of the Construct Driving the shRNA Expression.

The expression of E6 & E7, two major oncogenes in HPV-16 is driven by the common long control region (LCR). The expression status of these oncogenes is more in chorus with the enhancer than promoter as the promoter of HPV-16 is much weaker than the enhancer in driving their expression. shRNA was designed from the already tested siRNA1 sequence targeting the NF-1 binding site in HPV-16 enhancer to shut down the expression of both E6 and E7 simultaneously. We imparted tumour specificity to E6 & E7 gene silencing by governing the expression of shRNA under the influence of PLAP promoter and NFKB+PLAP enhancer-promoter chimera. Further the potential to knockdown E6 & E7 expression by these tissue specific constructs was compared with tissue non specific CMV viral promoter driving the shRNA expression.

All the constructs including tissue specific (PLAP-shRNA and NFκB+PLAP shRNA) and tissue non specific (CMV-shRNA) demonstrated selective silencing of E6 and E7 oncogenes in HPV-16 integrated cell lines SiHa and CaSki. These constructs caused no reduction of E6 and E7 in HPV-18 integrated cell line HeLa, illustrating the specificity of the shRNA against HPV-16 enhancer.

Figure 8:
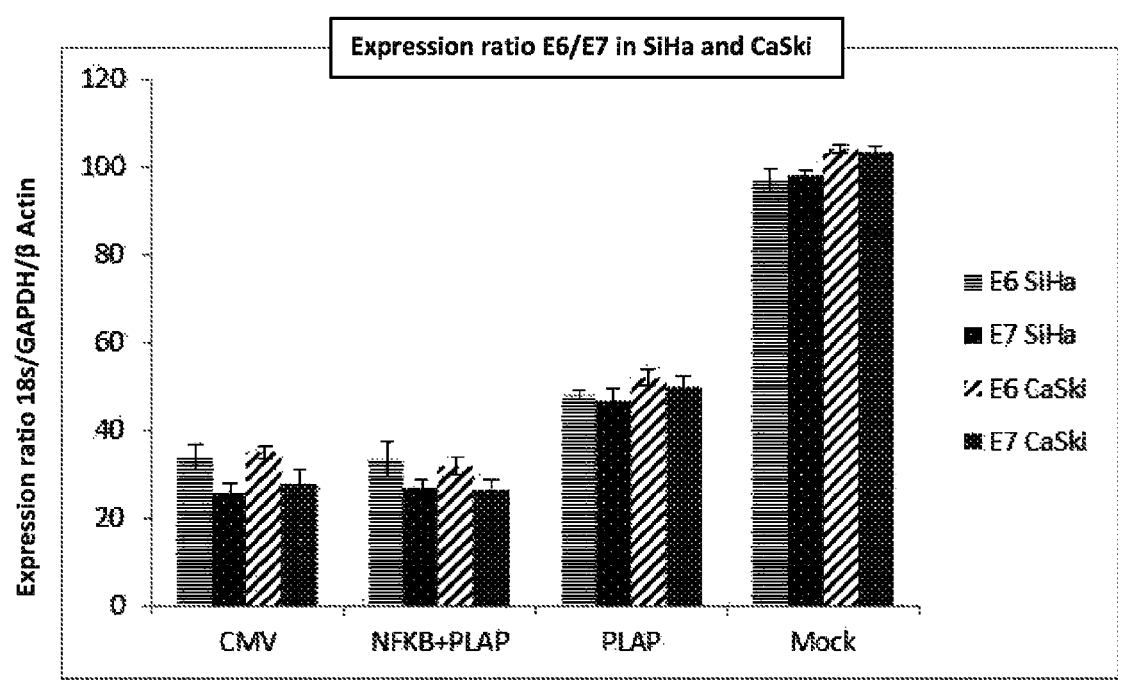
FIG. 8: Specificity of test shRNA towards HPV-16 enhancer. HPV-16 integrated cell lines (SiHa & CaSki) were transfected with various TGS inducing constructs (CMV shRNA, NFκB+PLAP shRNA& PLAP shRNA) and cell lines transfected with transfecting reagent alone served as mock. The fall in expression of E6 & E7 was evaluated by qPCR after normalization with three housekeeping genes (18s, GAPDH& β-actin). Decrease in E6 & E7 mRNA levels is seen in both HPV-16 positive cell lines SiHa and CaSki and the fall in expression is in concordance with strength of the therapeutic construct driving shRNA expression. The x-axes show different experiment groups (CMV-shRNA, NFκB+PLAP shRNA& PLAP shRNA), their negative controls & blank control; y-axes show the E6/E7 level, which was normalized to that of respective mock controls.

The decrease in mRNA expression of E6 & E7 as evaluated by Real Time PCR was dependent on the amplitude of the therapeutic construct driving the shRNA expression and the reduction in gene expression by tissue specific construct (NFκB+PLAP shRNA) was comparable to that of strong CMV viral promoter driving shRNA expression (CMV-shRNA) (FIG. 8).

Example 8

Regression in Expression of E6 & E7 Ameliorates Expression of p53 Targets in Both SiHa & CaSki Cell Lines.

Reduction in expression of E6 leads to activation of wild type p53 as shown by increase in expression levels of p53 target genes like Puma & Noxa at the transcriptional level. This was corroborated by a western blot which showed significant increase in level of p53 protein. This increase in expression of p53 and its target genes was in accordance with the strength of the constructs driving the shRNA expression (FIG. 9-10).

Example 8

MTT Assay:

For in vitro cytotoxicity analysis, the overnight-cultured cells ($5 \times 10^4$, per well in a 24-well plate) were transfected with various control or specific shRNA clones in triplicates. Cell survival was estimated 120 hours post transfection following standard MTT assay protocol.

Flow Cytometry:

Cells transfected with test and control shRNA clones were trypsinized, washed with PBS, and fixed overnight in 70% ethanol. Cells were then stained with propidium iodide (Sigma-Aldrich) and fluorescence was acquired using a BD FACS Flow Cytometer. Data was analyzed using WinMDI software available at http://pingu.salk.edu/software.html.

Suppression of E6 & E7 is Accompanied by Reduced Cell Proliferation and Apoptosis in Various HPV-16 In Vitro Models:

To examine weather decrease in expression of E6 & E7 affects cell growth, cellular morphology, proliferation and apoptosis was evaluated. Transfection of various test shRNA expressing constructs caused apoptotic morphology in SiHa and CaSki cells but no such changes were observed in scrambled and blank control cells.

Cell proliferation studies by MTT assay revealed that there was concomitant decrease in cellular proliferation in test shRNA transfected cells as compared to control shRNA treated cells and this diminution was in line with the strength of the therapeutic construct expressing shRNA (FIG. 11).

Flow cytometric analysis by PI staining demonstrated hike in the percentage of apoptotic cells in sub-G1 phase of cell cycle in test shRNA treated cells than scrambled shRNA & blank control cells and this proportion of hypo diploid cells was in direct agreement with the magnitude of the therapeutic construct expressing shRNA (FIG. 12).

Example 11 shRNA Elicits TGS by Methylation of Histone Tails and does not Impinge CpG Methylation.

TGS is caused either by DNA methylation or heterochromatization or by stalling the binding of RNA polymerase to pre initiation complex. To investigate the mechanism by which shRNA acted on the enhancer of HPV-16, we examined the effects on epigenetic marks reported to be involved in TGS.

Using chip assay, we assessed the level of histone H3K9 dimethylation (H3K9me2) and H3K27 trimethylation (H3K27me3), two repressive epigenetic marks shown to increase as a result of TGS. The levels of both these silent state heterochromatin markers were enriched at the targeted enhancer in test shRNA treated SiHa cells. Furthermore, treatment of SiHa cells with histone deacetylase (HDAC) inhibitor trichostatin (TSA) reduced this enrichment indicating that HDACs were likely to be involved in the process (FIG. 13A).

Bisulphite treatment of genomic DNA from both test and control shRNA transfected cells showed no change in the methylation status of the targeted region reflecting that the regression in expression of E6 & E7 by shRNA treatment is not due to DNA methylation (FIG. 13B).

Example 12

Design and Construction of Various Prodrug Activating Therapeutic Clones:

We used yeast cytosine deaminase gene (FCY1) for prodrug activation. FCY1 was amplified from yeast DNA following a nested PCR strategy. In the first round of PCR 900 bp sequence spanning the 5' and 3' flanking ends of the FCY1 region was amplified with requisite primers and in the second round the initial PCR product was used as template to amplify the coding cytosine deaminase (CD) region with another set of primers having Nco1 & Xba1 restriction sites incorporated. Luciferase inserted between Nco1 & Xba1 in promoter cloned PGL3-Basic as well as in enhancer-promoter cloned PGL3-Basic was replaced by ligating and cloning amplified FCY1 between these sites. To generate positive control for CD expression, luciferase in PGL3-control vector was replaced by FCY1 while as luciferase replaced by FCY1 in promoter less PGL3-Basic served as negative control.

Generation and Characterization of Various Tumour Specific Gene Suiciding Based Therapeutic Modalities:

Owing to the strong and cancer-specific transcriptional activity, the PLAP promoter and NFκB+PLAP enhancer-promoter cassettes were subjected to further study and used for generation of various (GDEPT) based therapeutic modalities. Yeast (S. cerevisiae), cytosine deaminase (CD) gene FCY1 was amplified and cloned downstream to promoter cloned PGL3-Basic or enhancer-promoter cloned PGL3-Basic by replacing the luciferase gene with CD gene, thus modifying PLAP-luc and NFKB+PLAP-luc into PLAP-CD & NFKB+PLAP-CD respectively. CD was also cloned downstream to robust tissue non-specific viral promoter SV40 in PGL3-Control (SV40-CD) to compare the compare the potency & specificity of our tumour specific therapeutic constructs, Promoter less CD served as negative control for GDEPT.

By restriction endonuclease digestion, it was authenticated that four target segments; PLAP promoter and NFKB+PLAP enhancer-promoter, SV40 promoter and CD were inserted correctly into PGL3-B/PGL3-C vectors respectively. The sequences of all inserted fragments in all the recombinant vectors were confirmed by sequencing from professional agencies (FIG. 14).

Example 13

Cytosine Deaminase Expression is Tumour Specific & Dependent Both on Dose and Strength of Prodrug Activation Machinery:

The specificity of various PLAP promoter/NFKB+PLAP enhancer promoter was illustrated by luciferase/GFP reporter assay systems. Once, this specificity was established they were used for the generation of various prodrug activating therapeutic modalities. This was accomplished by using these tissue specific enhancer/promoter systems for driving the expression of yeast CD. When, these GDEPT clones were transfected in PLAP positive cervical cancer cell line HeLa, the expression of CD both at mRNA & protein level was found to be dependent both on the amount as well as the strength of therapeutic modality driving the CD expression. The transcriptional/translational activity of NFKB–PLAP enhancer-promoter system (NFKB+PLAP-CD) was highly comparable to that of strong SV40 virus promoter (SV40-CD) (FIG. 15).

Example 14

Cytotoxicity Induced by Prodrug Activation was in Accordance with the Magnitude of the Therapeutic Modality Driving CD Expression:

To evaluate whether the expression of the CD gene could activate the prodrug 5-FC to active drug 5-FU and consequently induce cytotoxicity, cell survival effect of various GDEPT clones was determined. Prodrug activating therapeutic constructs were transistly transfected to various PLAP positive cervical cancer cell lines (HeLa), colon cancer cell line Caco-2 and non-PLAP non human cell line CHO. Cell cytotoxicity of various therapeutic constructs evaluated after addition of 5-FC was found to be dependent both on the amplitude of the therapeutic construct driving CD expression as well as the amount of prodrug (5-FC).

Figure 16A:
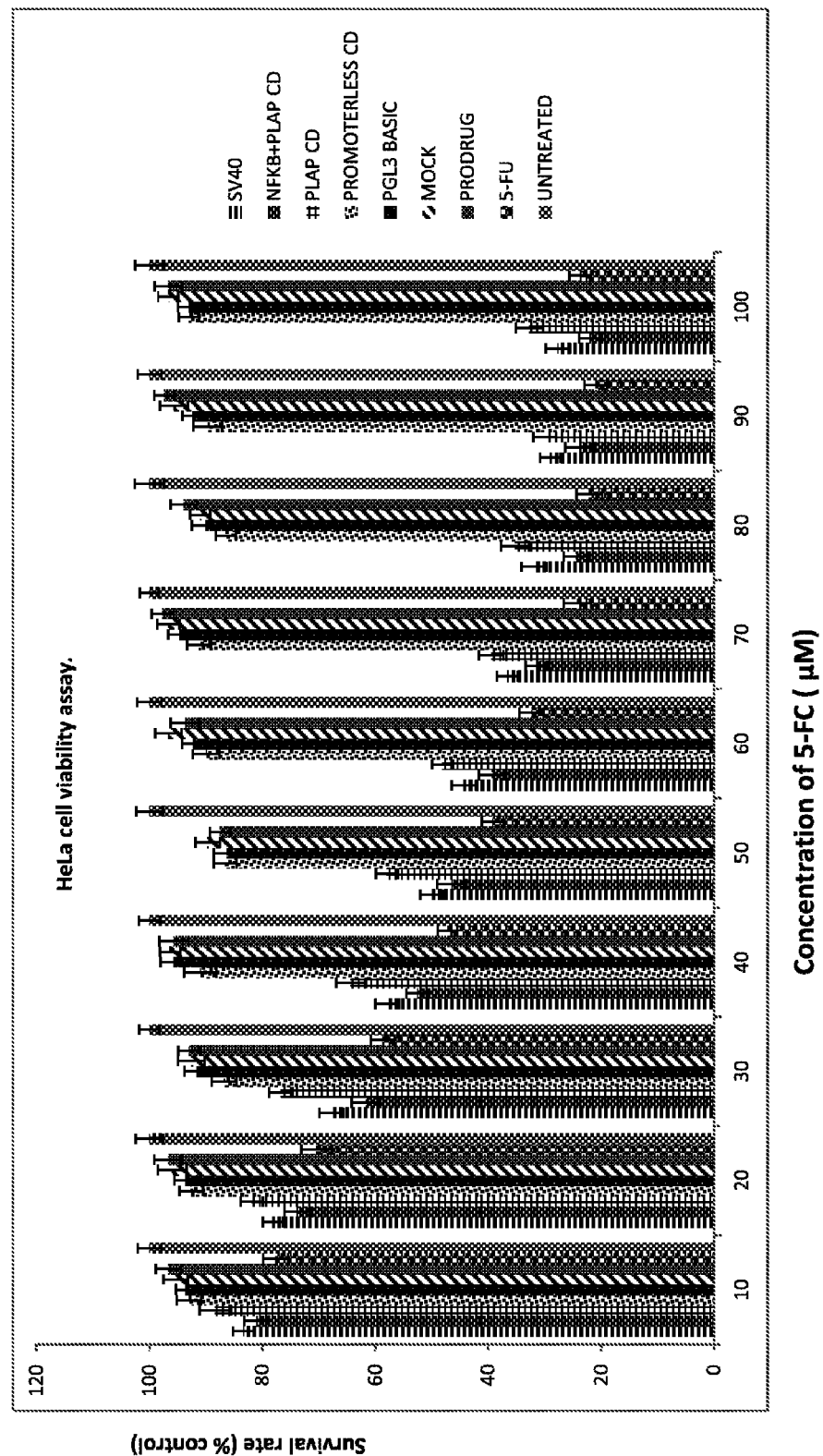
FIG. 16: Decrease in cell survival by various prodrug activation constructs: Cytotoxicity in PLAP positive and PLAP negative cell lines mediated by various gene suiciding therapeutic constructs. Each cell clone was seeded onto a 24 well plate at a density of 5×103 cells/well. Cells were transfected with various pro-drug activating therapeutic constructs and 48 hours post transfections varying amounts of 5-FC was added to each transfected well and 96 hours post prodrug addition cell viability was calculated by MTT. 5-FC was activated to 5-FU when either enhancer/promoter systems were used to drive CD expression and not in appropriate control systems (Promoterless CD, PGL3 Basic and Mock). The decrease in cell survival by cancer specific NFκB+PLAP enhancer-promoter system was at par with tissue non-specific strong viral promoter SV40.PLAP promoter/enhancer based therapeutic constructs decreased cell survival significantly only in PLAP positive in vitro models while as SV40 based therapeutic modalities produced cell killing even in PLAP negative cell line CHO. The data represent means of the cell viability, each performed in triplicate, and bars represent standard deviation.
Figure 16B:
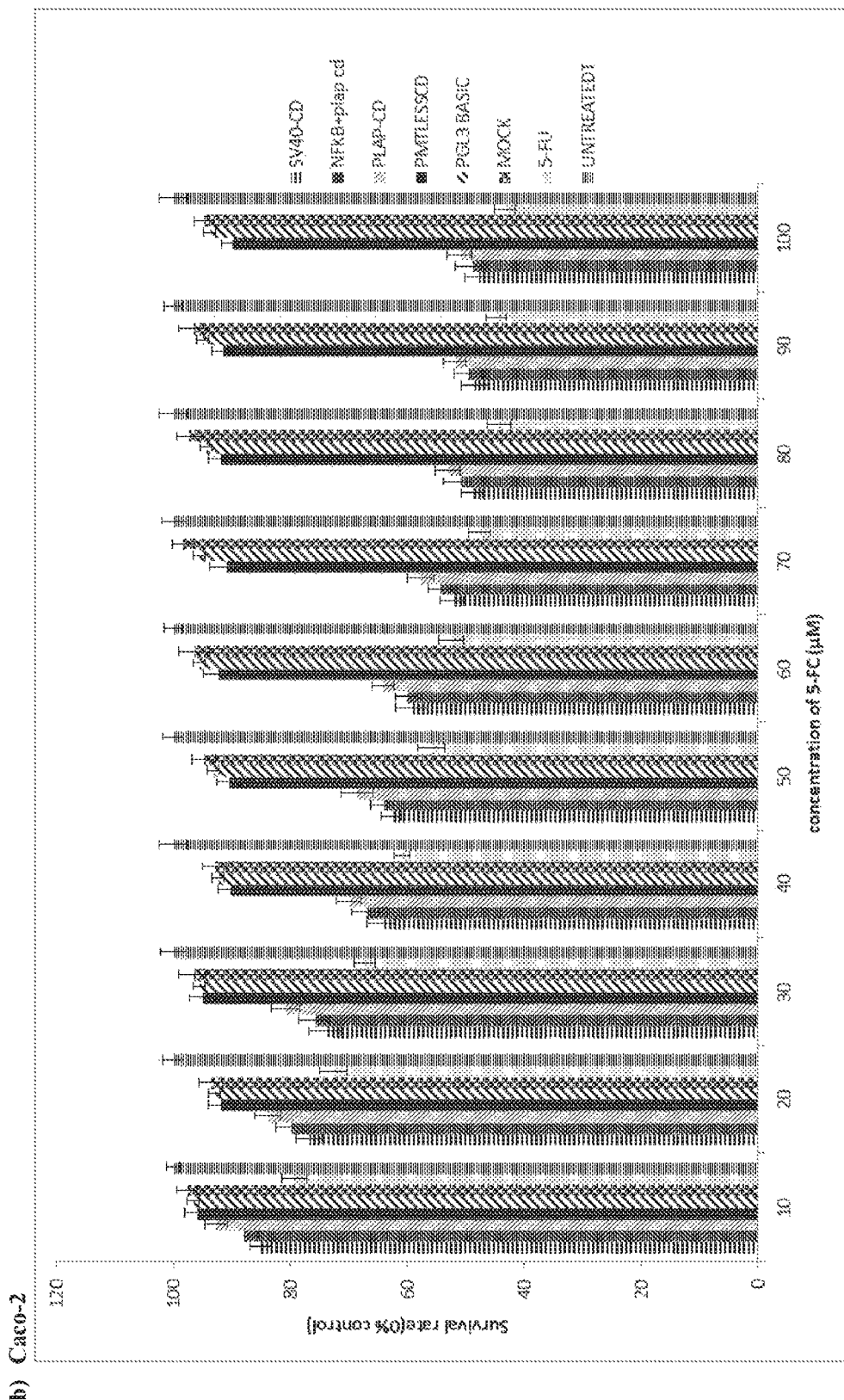
Figure 16C:
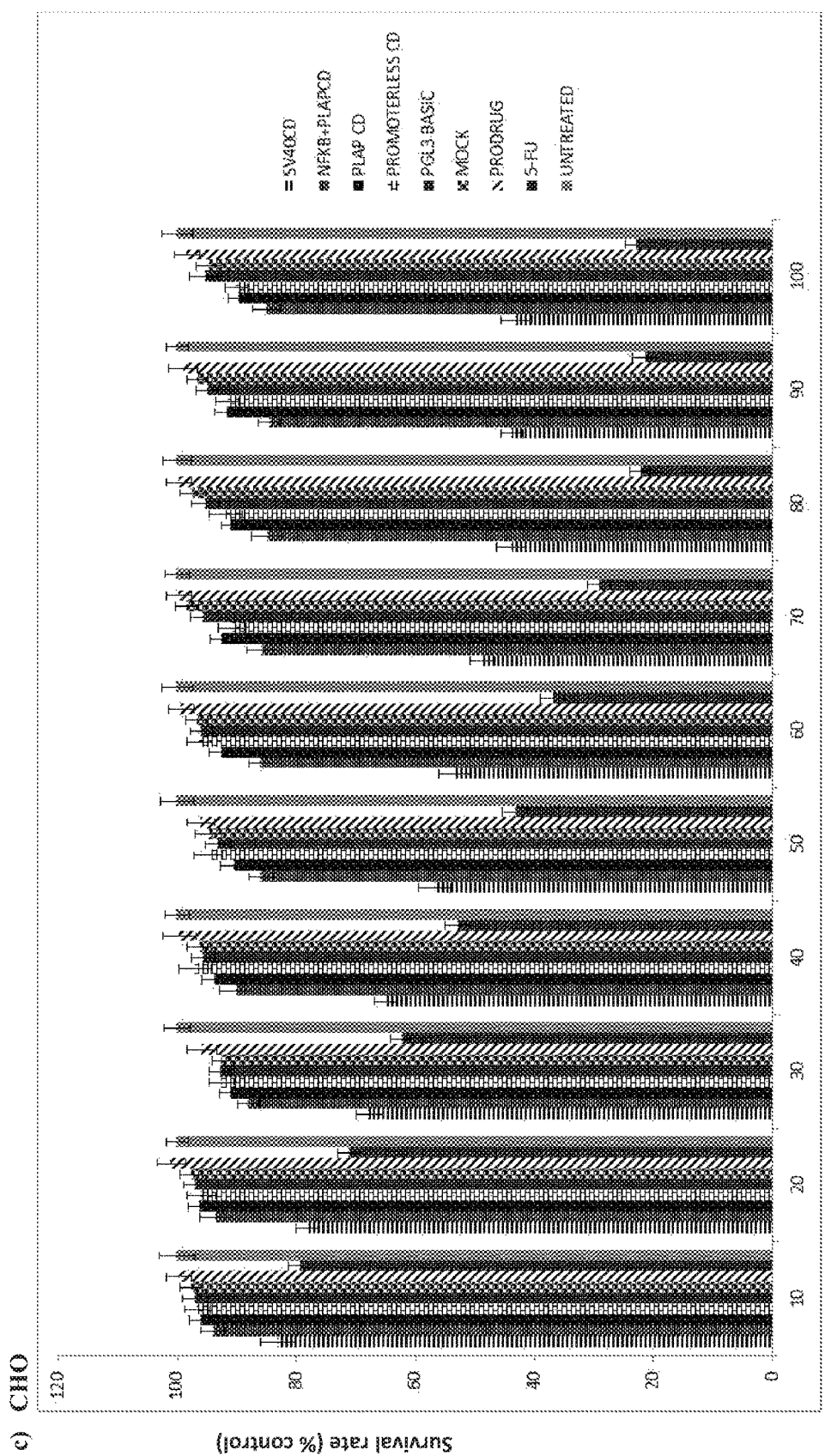

Cytotoxic effects produced by tissue specific PLAP promoter or NFκB+PLAP enhancer-promoter were highly specific and these therapeutic constructs induced cytotoxicity only in PLAP positive cells and not in non-PLAP cells demonstrating the tissue specificity of these GDEPT clones. Further, the decrease in cell survival by tissue specific enhancer-promoter based therapeutic modality (NFKB+PLAP-CD) was highly efficient and comparable to that strong tissue non-specific viral promoter based therapeutic construct (SV40-CD) (FIG. 16).

We claim:

1. A nucleic acid fusion construct consisting of SEQ ID NO: 1 and a tumor specific enhancer response element, wherein the tumor specific enhancer response element is selected from the group consisting of NFκB enhancer, Hypoxia inducible factor (HIF), and prostate specific antigen enhancer.

2. A nucleic acid fusion construct comprising SEQ ID NO: 1 and multiple repeats of the tumor specific enhancer response element wherein the tumor specific enhancer response element is selected from the group consisting of NFκB enhancer, Hypoxia inducible factor (HIF), prostate specific antigen enhancer, or artificial enhancers.

3. A nucleic acid fusion construct comprising SEQ ID NO: 1 and a tumor specific enhancer response element, wherein the tumor specific enhancer response element is NFκB enhancer response element.

4. A method of inhibiting or preventing or slowing down the growth of a cancer, tumor or neoplastic cell or tissue said method comprising administering to a subject a composition comprising a nucleic acid fusion construct as claimed in claim 1 along with a pharmaceutically acceptable carrier, wherein the nucleic acid fusion construct is linked to a therapeutic agent.

5. A vector comprising a nucleic acid fusion construct as claimed in claim 1.

6. A method of preparing a nucleic acid fusion vector of claim 5, the method comprising the steps of:
(a) isolating a cell or tissue specific promoter sequence having SEQ ID No. 1, and linking the SEQ ID No. 1 with an tumor specific enhancer response element sequence;
(b) inserting the nucleic acid fusion construct of step (a) into a vector; and
(c) obtaining a nucleic acid fusion vector.

7. A method as claimed in claim 6, wherein the tumor specific enhancer response element is selected from NFκB enhancer, Hypoxia inducible factor (HIF), and prostate specific enhancer.

8. A composition comprising a nucleic acid fusion construct according to claim 1 along with a pharmaceutically acceptable carrier.

9. A method of treatment said method comprising administering to a subject the composition as claimed in claim 8.

10. A kit comprising a first and a second component:
(a) wherein the first component consists of a nucleic acid fusion construct as recited in claim 1; and
(b) the second component is a prodrug.

11. The kit of claim 10, wherein the prodrug is activated by a therapeutic agent.

* * * * *